(12) United States Patent
Townsend et al.

(10) Patent No.: US 7,410,503 B2
(45) Date of Patent: *Aug. 12, 2008

(54) PROSTHETIC FOOT WITH TUNABLE PERFORMANCE

(75) Inventors: Barry W. Townsend, Bakersfield, CA (US); Byron K. Claudino, Bakersfield, CA (US)

(73) Assignee: Bioquest Prosthetics LLC, Bakersfield, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/814,155

(22) Filed: Apr. 1, 2004

(65) Prior Publication Data

US 2004/0186592 A1    Sep. 23, 2004

Related U.S. Application Data

(63) Continuation-in-part of application No. 10/473,682, filed as application No. PCT/US02/09589 on Mar. 29, 2002, which is a continuation-in-part of application No. 09/820,895, filed on Mar. 30, 2001, now Pat. No. 6,562,075, and a continuation-in-part of application No. 10/263,795, filed on Oct. 4, 2002, now Pat. No. 7,226,485, which is a continuation of application No. 09/820,895, filed on Mar. 30, 2001, now Pat. No. 6,562,075.

(51) Int. Cl.
 *A61F 2/66* (2006.01)
(52) U.S. Cl. ............... 623/53; 623/47; 623/49; 623/52; 623/55

(58) Field of Classification Search .......... 623/52, 623/55, 47, 48, 49, 50, 51, 53
See application file for complete search history.

(56) References Cited

U.S. PATENT DOCUMENTS 640,540 A    1/1900   Daniels
810,180 A    1/1906   Wintermute (Continued)

FOREIGN PATENT DOCUMENTS

CA    2103341 A1    4/1995

(Continued)

OTHER PUBLICATIONS

PCT Written Opinion from International Application No. PCT/US02/06901.

(Continued)

*Primary Examiner*—Corrine McDermott
*Assistant Examiner*—Javier G. Blanco
(74) *Attorney, Agent, or Firm*—Antonelli, Terry, Stout & Kraus, LLP.

(57) ABSTRACT

A prosthetic foot (147) has a longitudinally extending foot keel (149) and a resilient, monolithically formed calf shank (148) extending upwardly from the foot keel to form an ankle joint area of the prosthetic foot and a lower, prosthetic part of a leg above the ankle joint area for connection with a lower extremity prosthetic socket on a person's leg stump. At least the lower portion of the calf shank extending upwardly from the foot keel is anterior facing convexly curved. The shank and at least a portion of the foot keel are monolithically formed.

13 Claims, 30 Drawing Sheets

U.S. PATENT DOCUMENTS

| | | | |
|---|---|---|---|
| 2,453,969 A | 11/1948 | Carter |
| 3,335,428 A | 8/1967 | Gajdos |
| 4,555,817 A | 12/1985 | McKendrick |
| 4,645,509 A | 2/1987 | Poggie et al. |
| 4,721,510 A | 1/1988 | Cooper et al. |
| 4,822,363 A | 4/1989 | Phillips |
| 4,892,554 A | 1/1990 | Robinson |
| 4,911,724 A | 3/1990 | Fikes |
| 4,938,776 A | 7/1990 | Masinter |
| 4,959,073 A | 9/1990 | Merlette |
| 4,994,086 A | 2/1991 | Edwards |
| 5,019,109 A | 5/1991 | Voisin |
| 5,062,859 A | 11/1991 | Naeder |
| 5,066,305 A | 11/1991 | Firth |
| 5,112,356 A | 5/1992 | Harris et al. |
| 5,116,383 A | 5/1992 | Shorter et al. |
| 5,139,525 A | 8/1992 | Kristinsson |
| 5,156,632 A | 10/1992 | Wellershaus |
| 5,181,932 A | 1/1993 | Phillips |
| 5,181,933 A | 1/1993 | Phillips |
| 5,219,365 A | 6/1993 | Sabolich |
| 5,258,039 A | 11/1993 | Goh et al. |
| 5,290,319 A | 3/1994 | Phillips |
| 5,312,669 A | 5/1994 | Bedard |
| 5,314,499 A | 5/1994 | Collier, Jr. |
| 5,376,133 A | 12/1994 | Gramnas |
| 5,376,139 A | 12/1994 | Pitkin |
| 5,376,141 A | 12/1994 | Phillips |
| 5,387,246 A | 2/1995 | Phillips |
| 5,443,522 A | 8/1995 | Hiemisch |
| 5,443,527 A | 8/1995 | Wilson |
| 5,458,656 A | 10/1995 | Phillips |
| 5,482,513 A | 1/1996 | Wilson |
| 5,486,209 A | 1/1996 | Phillips |
| 5,507,838 A | 4/1996 | Chen |
| 5,509,936 A | 4/1996 | Rappoport et al. |
| 5,509,937 A | 4/1996 | Allard et al. |
| 5,509,938 A | 4/1996 | Phillips |
| 5,514,185 A | 5/1996 | Phillips |
| 5,545,230 A | 8/1996 | Kinsinger et al. |
| 5,549,714 A | 8/1996 | Phillips |
| 5,571,213 A | 11/1996 | Allen |
| 5,593,456 A | 1/1997 | Merlette |
| 5,593,457 A | 1/1997 | Phillips |
| 5,653,767 A | 8/1997 | Allen et al. |
| 5,653,768 A | 8/1997 | Kania |
| 5,695,526 A | 12/1997 | Wilson |
| 5,695,527 A | 12/1997 | Allen |
| 5,702,488 A | 12/1997 | Wood et al. |
| 5,725,598 A | 3/1998 | Phillips |
| 5,728,176 A | 3/1998 | Phillips |
| 5,728,177 A | 3/1998 | Phillips |
| 5,746,773 A | 5/1998 | Littig |
| 5,766,264 A | 6/1998 | Lundt |
| 5,776,205 A | 7/1998 | Phillips |
| 5,800,568 A | 9/1998 | Atkinson et al. |
| 5,800,569 A | 9/1998 | Phillips |
| 5,824,112 A | 10/1998 | Phillips |
| 5,897,594 A | 4/1999 | Martin et al. |
| 5,899,944 A | 5/1999 | Phillips |
| 5,944,760 A | 8/1999 | Christensen |
| 5,976,191 A | 11/1999 | Phillips |
| 5,993,488 A | 11/1999 | Phillips |
| 6,051,026 A | 4/2000 | Biedermann et al. |
| 6,071,313 A | 6/2000 | Phillips |
| 6,077,301 A | 6/2000 | Pusch |
| 6,083,265 A | 7/2000 | Shorter et al. |
| 6,099,572 A | 8/2000 | Mosler et al. |
| 6,187,052 B1 | 2/2001 | Molino et al. |
| 6,197,066 B1 | 3/2001 | Gabourie |
| 6,206,932 B1 | 3/2001 | Johnson |
| 6,206,934 B1 | 3/2001 | Phillips |
| 6,228,043 B1 | 5/2001 | Townsend et al. |
| 6,241,776 B1 | 6/2001 | Christensen |
| 6,270,468 B1 | 8/2001 | Townsend et al. |
| 6,280,479 B1 | 8/2001 | Phillips |
| 6,290,730 B1 | 9/2001 | Pitkin et al. |
| 6,350,286 B1 | 2/2002 | Atkinson et al. |
| 6,402,790 B1 | 6/2002 | Celebi |
| 6,406,500 B1 | 6/2002 | Phillips |
| 6,443,995 B1 | 9/2002 | Townsend et al. |
| 6,514,293 B1 | 2/2003 | Jang et al. |
| 6,527,811 B1 | 3/2003 | Phillips |
| 6,562,075 B2 | 5/2003 | Townsend et al. |
| 6,602,295 B1 | 8/2003 | Doddroe et al. |
| 6,663,673 B2 | 12/2003 | Christensen |
| 2002/0040249 A1 | 4/2002 | Phillips |
| 2002/0077706 A1 | 6/2002 | Phillips |
| 2002/0087216 A1 | 7/2002 | Atkinson et al. |
| 2002/0116072 A1 | 8/2002 | Rubie et al. |
| 2002/0133237 A1 | 9/2002 | Christesen |
| 2003/0009238 A1 | 1/2003 | Whayne |
| 2003/0028256 A1 | 2/2003 | Townsend et al. |
| 2003/0045944 A1 | 3/2003 | Mosler et al. |
| 2003/0093158 A1 | 5/2003 | Phillips et al. |
| 2003/0120354 A1 | 6/2003 | Doddroe et al. |
| 2003/0191540 A1 | 10/2003 | Townsend et al. |

FOREIGN PATENT DOCUMENTS

| | | |
|---|---|---|
| DE | 325171 C1 | 10/1920 |
| DE | 19717298 C1 | 5/1998 |
| DE | 298 20 904 U1 | 6/1999 |
| DE | 298 23 435 U1 | 9/1999 |
| DE | 29920434 U1 | 5/2000 |
| DK | EP 0 648 479 A1 | 10/1993 |
| EP | 0 331 468 | 9/1989 |
| EP | 0 648 479 A1 | 4/1995 |
| EP | 0793949 A1 | 9/1997 |
| FR | 2 640 499 A1 | 6/1990 |
| FR | 2 734 151 | 11/1996 |
| FR | 2734151 | 11/1996 |
| GB | 2 173 569 | 10/1986 |
| JP | 9-327473 | 12/1997 |
| JP | 11-299815 | 11/1999 |
| WO | WO 91/00070 | 1/1991 |
| WO | WO 94/10942 | 5/1994 |
| WO | WO 97/17042 | 5/1997 |
| WO | WO 00/71061 A1 | 11/2000 |
| WO | WO 02/02034 A1 | 1/2002 |
| WO | WO 02/30340 | 4/2002 |

OTHER PUBLICATIONS

International Search Report from International Application No. PCT/US01/48954.

International Search Report (Apr. 2002); International application No. PCT/US02/09573.

International Search Report (Jul. 1998); International application No. PCT/US02/30471.

International Search Report in corresponding PCT application No. PCT/US02/09571 dated Sep. 27, 2002.

International Search Report in corresponding PCT application No. PCT/US02/09589 dated Sep. 11, 2002.

Perry J. and Shanfield S., Efficiency of Dynamic Elastic Response Prosthetic Feet; Gait Initiation in Below-Knee Amputees: Analysis of Safe Function; Biomechanical Evaluation of Energy-Storing Prosthetic Feet, J. Rehabilitation Research and Development Service (Project #A517-RA), 1990, pp. 37, 38 & 44.

Barth, D.G., Schumacher, L. and Thomas, S.S., Gait Analysis and Energy Cost of Below-Knee Amputees Wearing Six Different Prosthetic Feet, JPO: Journal of Prosthetics and Orthotics, 1992, vol. 4, No. 2, pp. 626-638.

Menard, M.R. and Murray D.D., Subjective and Objective Analysis of an Energy-Storing Prosthetic Foot, Journal of Prosthetics and Orthotics, 1989, vol. 1, No. 4, pp. 173-183.

Menard, M.Ry-Storing Prosthetic Feet, Archives of Physical Medicine and Rehabilitation, May 1992, vol. 73, pp. 451-458.

Prince, F., Winter, D.A. et al., Mechanical Efficiency During Gait of Adults with Transtibial Amputation: A Pilot Study Comparing the SACH, Seattle, and Golden-Ankle Prosthetic Feet, Journal of Rehabilitation Research and Development, Jun. 1998, vol. 35, No. 2, pp. 177-185.

Winter, D.A., Biomechanics of Human Movement, John Wiley & Sons, Inc. 1979, pp. 61, 117-121.

Mann, R.A. and Hagy, J.L., The Function of the Toes in Walking, Jogging and Running, J.J.B. Lippincott Company, 1979, vol. 142, pp. 24-29.

Perry, J., Gait Analysis: Normal and Pathological Function, SLACK Incorporated, Thorofare, NJ, 1992, Chapter 4: Ankle Foot Complex, Chapter 19: Ground Reaction Force and Vector Analysis, Chapter 21: Energy Expenditure.

Valmassy, R.L., Clinical Biomechanics of the Lower Extremities, Mosby, 1996, Chaper 1: Lower Extremity Function and Normal Mechanics.

Hsu, M. and Nielsen, D., et al., Physiological Measurements of Walking and Running in People with Transtibial Amputations With 3 Different Prostheses, Journal of Othopaedic & Sports Physical Therapy, Sep. 1999; vol. 29, No. 9, pp. 527-533.

Macfarlane, P.A. and Nielsen, D.H. et al., Gait Comparisons for Below-Knee Amputees Using a Flex-Foot™ Versus a Conventional Prosthetic Foot, Journal of Prosthetics and Orthotics, 1991, vol. 3, No. 4, pp. 526-537.

Neilson, D.H. and Shurr, D.G. et al., Comparison of Energy Cost and Gait Efficiency During Ambulation in Below-Knee Amputees Using Different Prosthetic Feet—A Preliminary Report, Journal of Prosthetics and Orthotics, 1988, vol. 1, No. 1, pp. 24-31.

Macfarlane, P.A. and Nielsen, D.H. et al., Perception of Walking Difficulty by Below-Knee Amputees Using a Conventional Foot Versus the Flex-Foot, Journal of Prosthetics and Orthotics, 1991, vol. 3, No. 3, pp. 503-508.

Childress, D., Mechanical Properties of Prosthetic and Human Feet: From Shoes to Computer Alignment, $2^{nd}$ Conference of Advanced Prosthetics, Apr. 2002.

Wirta, R.W. et al., Effect on Gait Using Various Prosthetic Ankle-Foot Devices, Journal of Rehabilitation Research and Development, 1991, vol. 28, No. 2, pp. 13-24.

Winter, D.A. and Patia A.E. et al., Biomechanical Walking Pattern Changes in the Fit and Healthy Elderly, Physical Therapy, Jun. 1990, vol. 70, No. 6, pp. 340/15-346/21.

Ayyappa, E., Normal Human Locomotion, Part 1 : Basic Concepts and Terminology, Journal of Prosthetics and Orthotics, Winter 1997, vol. 9, No. 1, pp. 10-17.

Ayyapa, E., Normal Human Locomotion, Part 2: Motion, Ground-Reaction Force and Muscle Activity, Journal of Prosthetics and Orthotics, Spring 1997, vol. 9, No. 2, pp. 49-57.

Winter, D.A., Biomechanics and Motor Control of human Movement, University of Waterloo, John Wiley & Sons, Inc., 1990, Chapter 7.

J.B. Saunders, et al., The Major Determinants in Normal and Pathological Gait, Journal of Bone and Joint Survey, Jul. 1953, vol. 35A, No. 3, pp. 543-558.

Komi, P.V., Stength and Power in Sport, Blackwell Scientific Publications, 1992, Chapter 6B, pp. 115-129.

McComas, A.J., Skeletal Muscle Form and Function, Human Kinetics, Champaign, IL, 1996, pp. 326-375.

Mattes, S.J., et al., Walking Symmetry and Energy Cost in Persons with Unilateral Transtibial Amputations: Matching Prosthetic and Intact Limb Inertial Properties, Archives of Physical Medicine and Rehabilitation, May 2000, vol. 81, pp. 561-568.

Bojsen-Moller, F., Calcaneocuboid Joint and Stability of the Longitudinal Arch of the Foot at High and Low Gear Push Off, Journal of Anatomy, Aug.-Dec. 1979, vol. 129, pp. 165-176.

Hicks, J.H., The Mechanics of the Foot, The Plantar Aponeurosis and the Arch, Journal of Anatomy, 1954, vol. 88, Pt. 1, pp. 25-31.

Brunnstrom, S. (revised by R. Dickinson), Clinical Kinesiology, F.A. Davis Company, Philadelphia, 1972, pp. 35.

Stiehl, J., Inman's Joints of the Ankle ($2^{nd}$ Ed.), Williams & Wilkins, Baltimore, MD, 1991, p. 39.

Bateni, H., et al.., Kinematic and Kinetic Variations of Below-Knee Amputee Gait, Prosthetic and Orthotic Science, 2002, vol. 14, No. 1, pp. 2-10.

International Search Report; PCT/US03/09506; filed Mar. 31, 2003.

2003 Ossur Product Catalog; TALUX™; pp. 179-181.

International Search Report; PCT/US05/11304 ; Filing Date : Apr. 1, 2005.

International Search Report; PCT/US05/11291; Filing Date: Apr. 1, 2005.

Supplementary Partial European Search Report; EP 02 75 7836; Date : Mar. 7, 2006.

Supplementary Partial European Search Report; EP 02 71 3785; Date : Mar. 7, 2006.

International Search Report; PCT/US05/34037; Filing Date: Sep. 26, 2005.

Supplementary European Search Report; EP 02 71 3785; May 22, 2006.

Supplementary European Search Report; EP 02 75 7836; May 25, 2006.

International Search Report; International Application No. PCT/US05/10583; Date of Mailing: Apr. 5, 2006.

Written Opinion of the International Searching Authority; International Application No. PCT/US05/10583; International Filing Date: Mar. 30, 2005.

Office Action of U.S. Appl. No. 10/408,107; mailed Mar. 7, 2007.

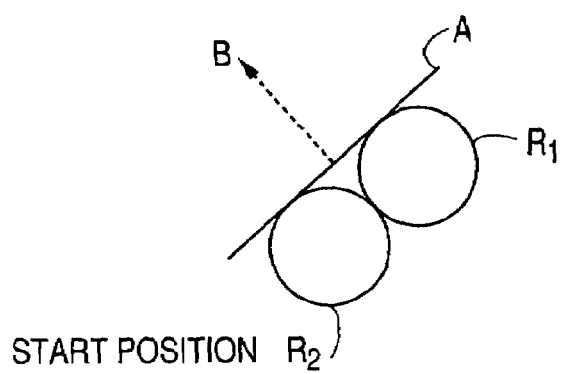
FIG. 1
START POSITION
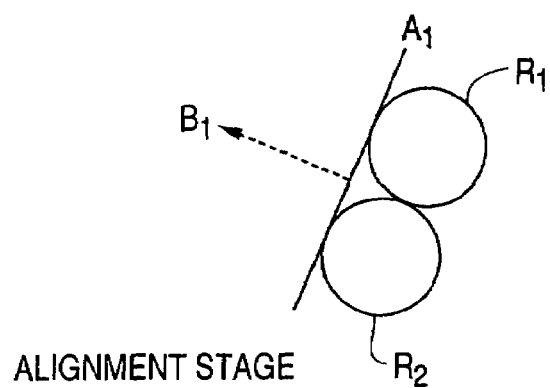
FIG. 2
ALIGNMENT STAGE
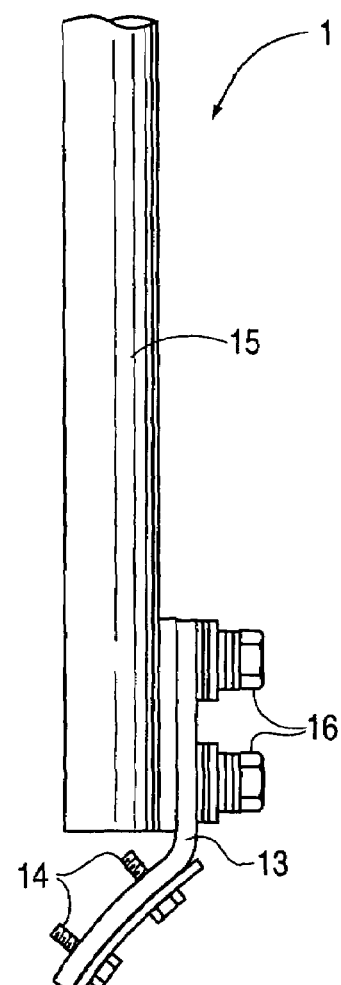
FIG. 3
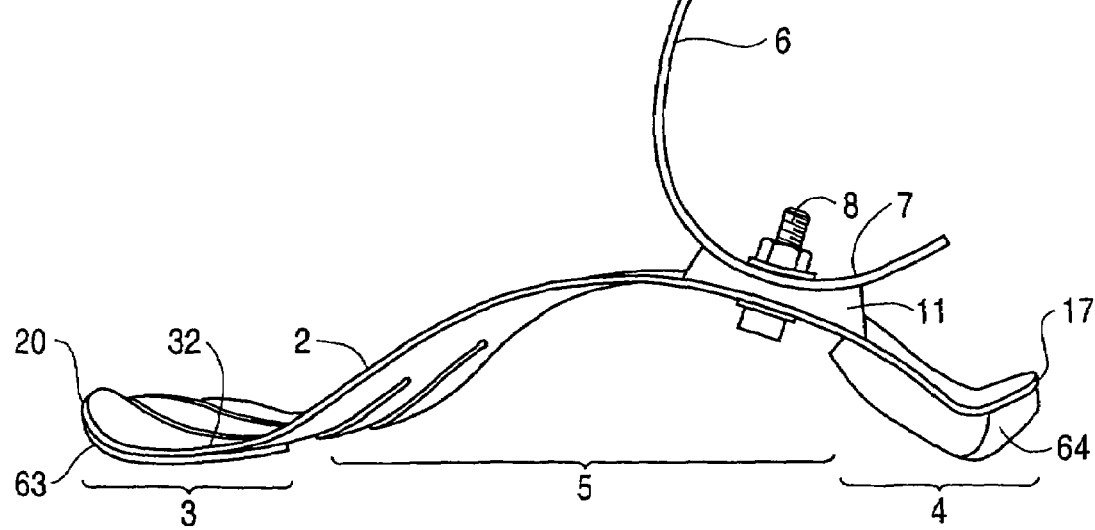

50

51

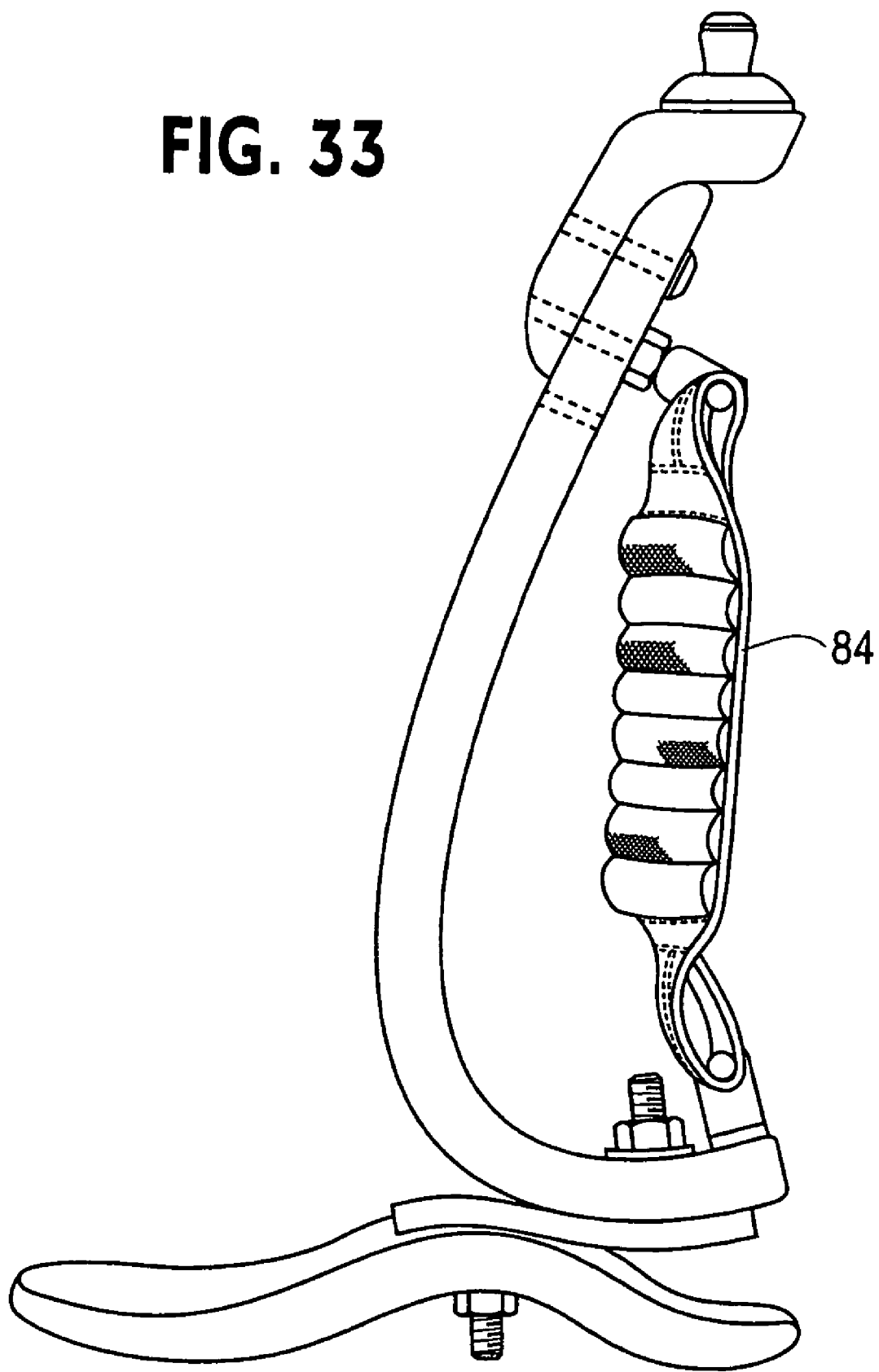

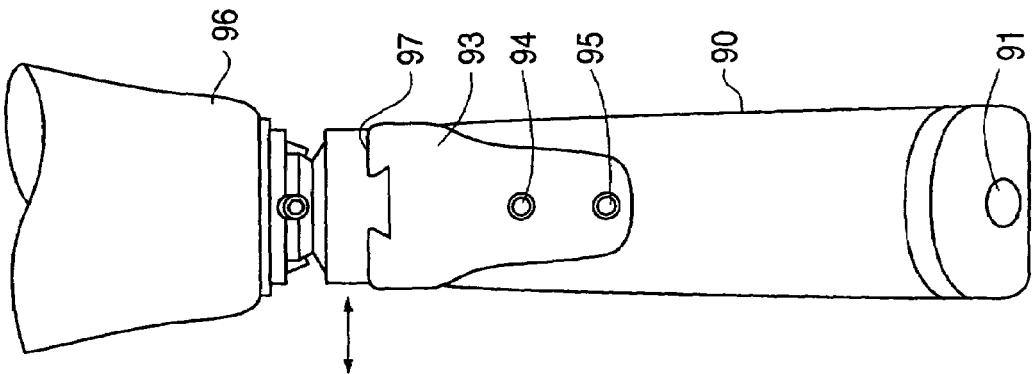
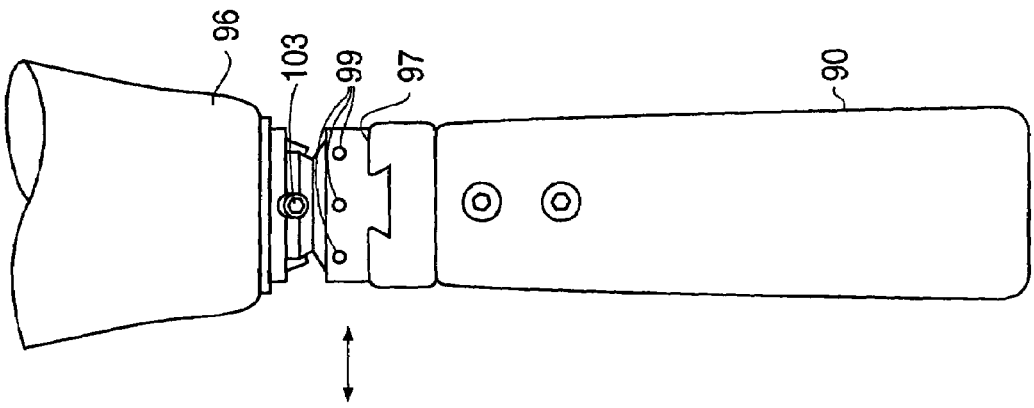
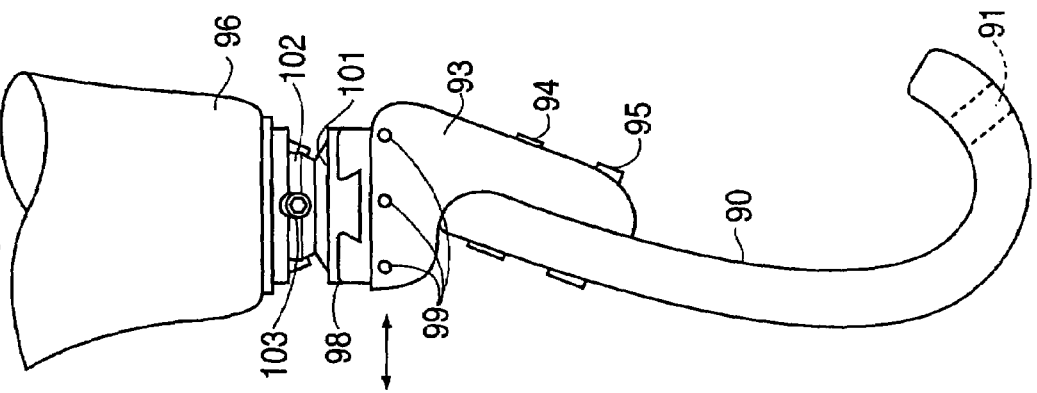

PROSTHETIC FOOT WITH TUNABLE PERFORMANCE

RELATED APPLICATIONS

This application is a continuation in part of application Ser. No. 10/473,682, which is the U.S. national designated filing under 35 U.S.C. §371 of international application PCT/US02/09589 filed Mar. 29, 2002, which is a continuation in part of U.S. application Ser. No. 09/820,895, filed Mar. 30, 2001 and now U.S. Pat. No. 6,562,075 issued May 13, 2003, the priority of which is claimed. This application is also a continuation in part of application Ser. No. 10/263,795 filed Oct. 4, 2002, now U.S. Pat. No. 7,226,485 which is a continuation of U.S. application Ser. No. 09/820,895, filed Mar. 30, 2001 and now U.S. Pat. No. 6,562,075 issued May 13, 2003, the priority of which is claimed.

TECHNICAL FIELD

The present invention relates to a high performance prosthetic foot providing improved dynamic response capabilities as these capabilities relate to applied force mechanics.

BACKGROUND ART

A jointless artificial foot for a leg prosthesis is disclosed by Martin et al. in U.S. Pat. No. 5,897,594. Unlike earlier solutions wherein the artificial foot has a rigid construction provided with a joint in order to imitate the function of the ankle, the jointless artificial foot of Martin et al. employs a resilient foot insert which is arranged inside a foot molding. The insert is of approximately C-shaped design in longitudinal section, with the opening to the rear, and takes up the prosthesis load with its upper C-limb and via its lower C-limb transmits that load to a leaf spring connected thereto. The leaf spring as seen from the underside is of convex design and extends approximately parallel to the sole region, forward beyond the foot insert into the foot-tip region. The Martin et al. invention is based on the object of improving the jointless artificial foot with regard to damping the impact of the heel, the elasticity, the heel-to-toe walking and the lateral stability, in order thus to permit the wearer to walk in a natural manner, the intention being to allow the wearer both to walk normally and also to carry out physical exercise and to play sports. However, the dynamic response characteristics of this known artificial foot are limited. There is a need for a higher performance prosthetic foot having improved applied mechanics design features which can improve amputee athletic performances involving activities such as running, jumping, sprinting, starting, stopping and cutting, for example.

Other prosthetic feet have been proposed by Van L. Phillips which allegedly provide an amputee with an agility and mobility to engage in a wide variety of activities which were precluded in the past because of the structural limitations and corresponding performances of prior art prostheses. Running, jumping and other activities are allegedly sustained by these known feet which, reportedly, may be utilized in the same manner as the normal foot of the wearer. See U.S. Pat. Nos. 6,071,313; 5,993,488; 5,899,944; 5,800,569; 5,800,568; 5,728,177; 5,728,176; 5,824,112; 5,593,457 5,514,185; 5,181,932; and 4,822,363, for example.

DISCLOSURE OF INVENTION

In order to allow the amputee athlete to attain a higher level of performance, there is a need for a high performance prosthetic foot having improved applied mechanics, which foot can out perform the human foot and also out perform the prior art prosthetic feet. It is of interest to the amputee athlete to have a high performance prosthetic foot having improved applied mechanics, high low dynamic response, and alignment adjustability that can be fine tuned to improve the horizontal and vertical components of activities which can be task specific in nature.

The prosthetic foot of the present invention addresses these needs. According to an example embodiment disclosed herein, the prosthetic foot of the invention comprises a longitudinally extending foot keel having a forefoot portion at one end, a hindfoot portion at an opposite end and a relatively long midfoot portion extending between and upwardly arched from the forefoot and hindfoot portions. A calf shank including a downward convexly curved lower end is also provided. An adjustable fastening arrangement attaches the curved lower end of the calf shank to the upwardly arched midfoot portion of the foot keel to form an ankle joint area of the prosthetic foot.

The adjustable fastening arrangement permits adjustment of the alignment of the calf shank and the foot keel with respect to one another in the longitudinal direction of the foot keel for tuning the performance of the prosthetic foot. By adjusting the alignment of the opposed upwardly arched midfoot portion of the foot keel and the downward convexly curved lower end of the calf shank with respect to one another in the longitudinal direction of the foot keel, the dynamic response characteristics and motion outcomes of the foot are changed to be task specific in relation to the needed/desired horizontal and vertical linear velocities. A multi-use prosthetic foot is disclosed having high and low dynamic response capabilities, as well as biplanar motion characteristics, which improve the functional outcomes of amputees participating in sporting and/or recreational activities. A prosthetic foot especially for sprinting is also disclosed.

The prosthetic foot can also include a device to limit the extent of the motion of the upper end of the calf shank in response to force loading and unloading the calf shank during use of the prosthetic foot. In one embodiment, the device is a piston-cylinder unit connected between the upper and lower ends of the calf shank and containing at least one pressurized fluid to limit the extent of motion and also dampen the energy being stored or released during calf shank compression and expansion. In other embodiments the posterior calf device stores its own potential energy during force loading of the prosthesis and returns the stored energy during force unloading to add to the total elastic energy storage capabilities thereby increasing the kinetic power generated for propulsive force by the prosthetic foot in gait.

These and other objects, features and advantages of the present invention become more apparent from a consideration of the following detailed description of disclosed example embodiments of the invention and the accompanying drawings.

BRIEF DESCRIPTION OF THE DRAWINGS

FIG. 1 is a schematic illustration representing the two adjacent radii of curvatures $R_1$ and $R_2$, one against the other, of a foot keel and calf shank of a prosthetic foot of the invention which creates a dynamic response capability and motion outcome of the foot in gait in the direction of arrow B which is perpendicular to the tangential line A connecting the two radii.

FIG. 2 is a view similar to FIG. 1 but showing the alignment of the two radii having been changed in the prosthetic foot according to the invention to increase the horizontal component and decrease the vertical component of the dynamic response capability and motion outcome of the foot in gait so that arrow $B_1$, perpendicular to tangential line $A_1$, is more horizontally directed than is the case depicted in FIG. 1.

FIG. 3 is a side view of a prosthetic foot according to an example embodiment of the invention with pylon adapter and pylon connected thereto for securing the foot to the lower leg of an amputee.

FIG. 33 is a side view of a still further example embodiment of the prosthetic foot like that in FIGS. 28-32 except that a flexible strap is used to limit only the extent of expansion motion of the upper end of the calf shank.

FIG. 34 is a side view of another embodiment of the prosthetic foot with an alignment coupler device located on an adapter connected to the upper end of the calf shank for securing the foot to a prosthetic socket attached to an amputee's leg, the alignment coupler device allowing medial-lateral and anterior-posterior sliding adjustment of the foot relative to the prosthetic socket.

FIG. 35 is a front view of the prosthetic foot of FIG. 34, as seen from the left side of the foot as shown in FIG. 34.

FIG. 36 is a rear view of the prosthetic foot of FIG. 34, as seen from the right side of the foot in FIG. 34.

DETAILED DESCRIPTION OF EMBODIMENTS

Figure 4:
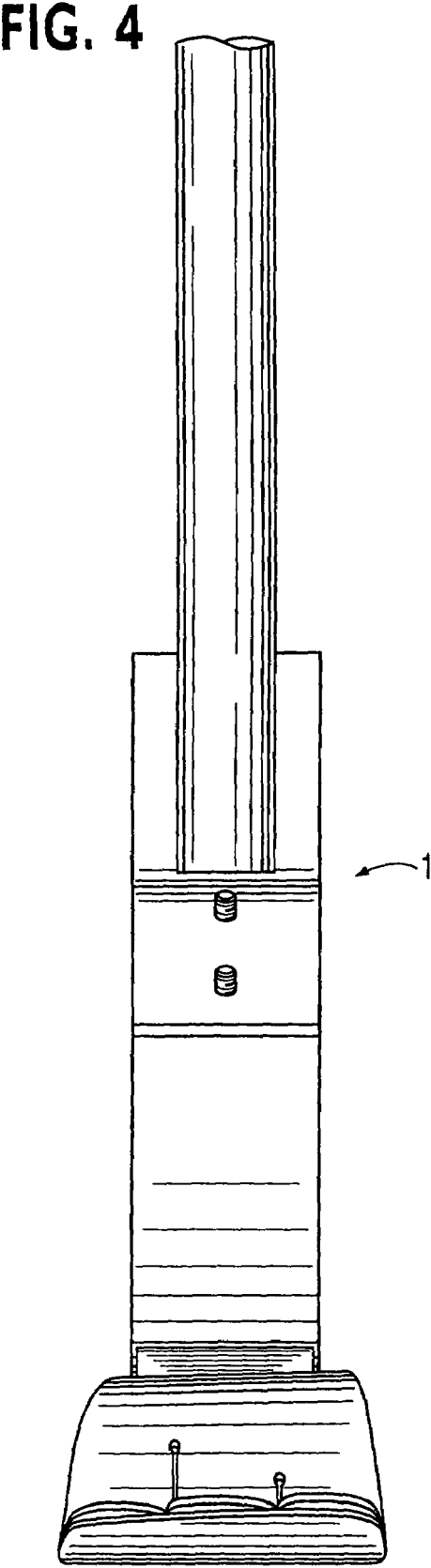
FIG. 4 is a front view of the prosthetic foot with pylon adapter and pylon of FIG. 3.
Figure 5:
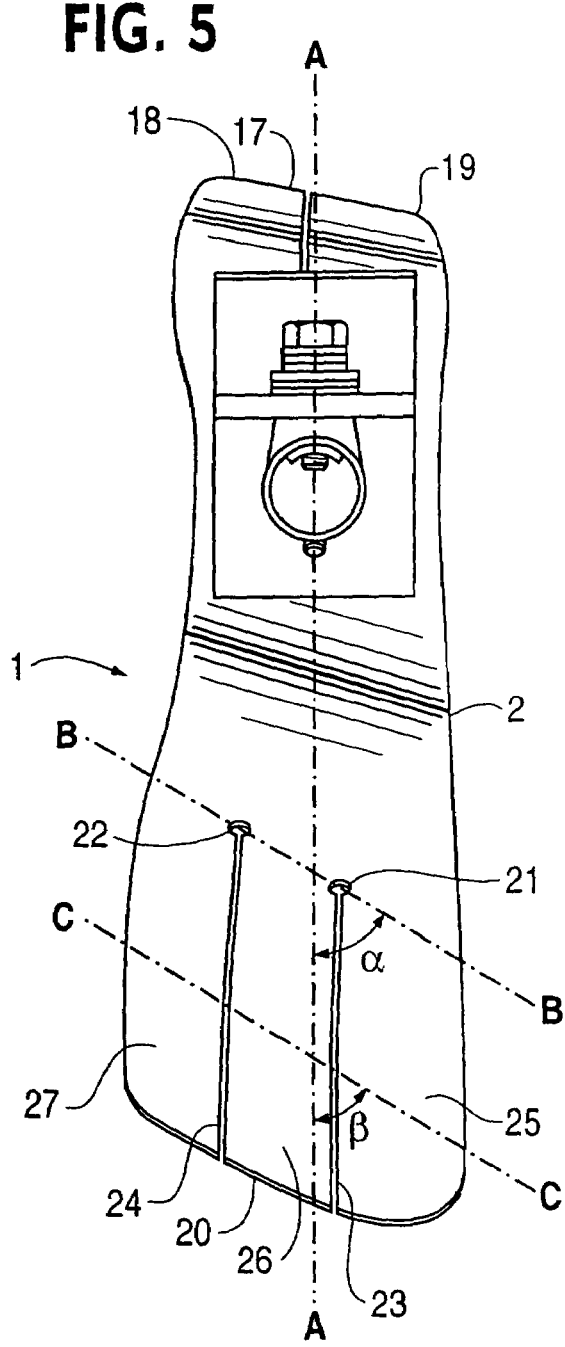
FIG. 5 is a top view of the embodiment of FIGS. 3 and 4.

Referring now to the drawings, a prosthetic foot 1 in the example embodiment of FIGS. 3-5 is seen to comprise a longitudinally extending foot keel 2 having a forefoot portion 3 at one end, a hindfoot portion 4 at an opposite end and an upwardly arched midfoot portion 5 extending between the forefoot and hindfoot portions. The midfoot portion 5 is upward convexly curved over its entire longitudinal extent between the forefoot and hindfoot portions in the example embodiment.

An upstanding calf shank 6 of the foot 1 is attached at a portion of a downward convexly curved lower end 7 thereof to a proximate, posterior surface of the keel midfoot portion 5 by way of a releasable fastener 8 and coupling element 11. The fastener 8 is a single bolt with nut and washers in the example embodiment, but could be a releasable clamp or other fastener for securely positioning and retaining the calf shank on the foot keel when the fastener is tightened.

Figure 8:
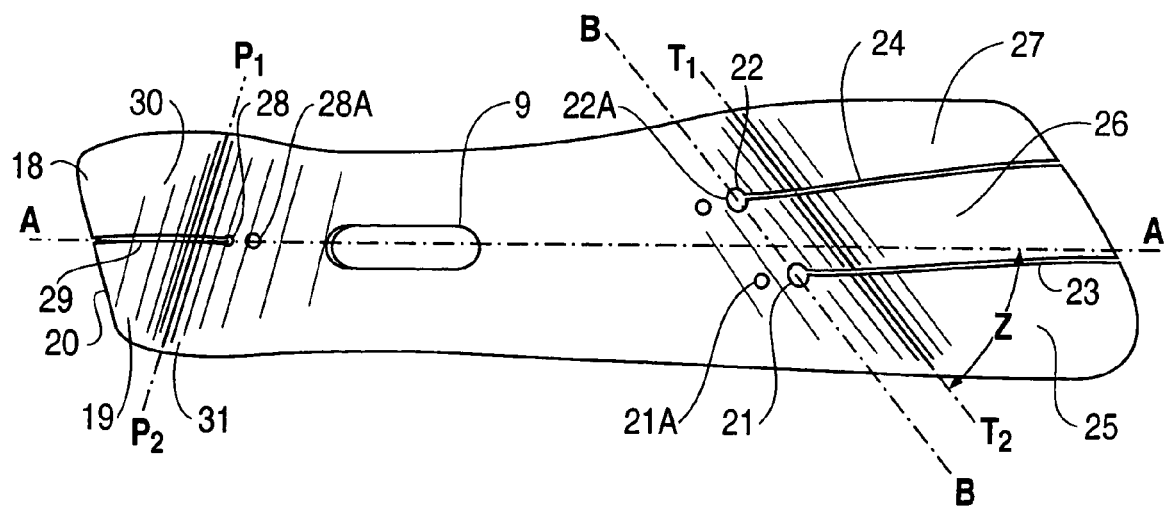
FIG. 8 is a bottom view of the foot keel in the prosthetic foot in FIG. 3 which. provides high low dynamic response characteristics as well as biplanar motion capabilities.
Figure 15:
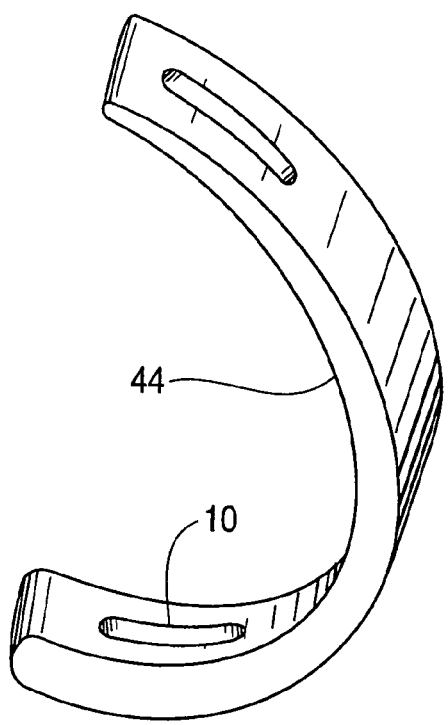
FIG. 15 is a side view from slightly above and to the front of a parabola shaped calf shank of the prosthetic foot of the invention, the thickness of the calf shank tapering toward its upper end.

A longitudinally extending opening 9 is formed in a proximate, posterior surface of the keel midfoot portion 5, see FIG. 8. A longitudinally extending opening 10 is also formed in the curved lower end 7 of the calf shank 6 like that shown in FIG. 15, for example. The releasable fastener 8 extends through the openings 9 and 10 which permit adjusting the alignment of the calf shank and the foot keel with respect to one another in the longitudinal direction, A-A in FIG. 5, when the fastener 8 is loosened or released for tuning the performance of the prosthetic foot to be task specific. Thus, the fastener 8, coupling element 11 and longitudinally extending openings 9 and 10 constitute an adjustable fastening arrangement for attaching the calf shank to the foot keel to form an ankle joint area of the prosthetic foot.

The effects of adjusting the alignment of the calf shank 6 and foot keel 2 are seen from a consideration of FIGS. 1 and 2, wherein the two radii $R_1$ and $R_2$, one next to another, represent the adjacent, facing, domed or convexly curved surfaces of the foot keel midportion 5 and the calf shank 6. When two such radii are considered one next to another, motion capability exists perpendicular to a tangential line, A in FIG. 1, $A_1$ in FIG. 2, drawn between the two radii. The interrelationship between these two radii determines a direction of motion outcomes. As a consequence, dynamic response force application of the foot 1 is dependent on this relationship. The larger the radius of a concavity, the more dynamic response capability. However, the tighter a radius, the quicker it responds.

The alignment capability of the calf shank and foot keel in the prosthetic foot of the invention allows the radii to be shifted so that horizontal or vertical linear velocities with the foot in athletic activities are affected. For example, to improve the horizontal linear velocity capability of the prosthetic foot 1, an alignment change can be made to affect the relationship of the calf shank's radius and the foot keel radius. That is, to improve the horizontal linear velocity characteristic, the bottom radius $R_2$, of the foot keel, is made more distal than its start position, FIG. 2 as compared with FIG. 1. This changes the dynamic response characteristics and motion outcomes of the foot 1 to be more horizontally directed and as a result greater horizontal linear velocity can be achieved with the same applied forces.

Figure 23:
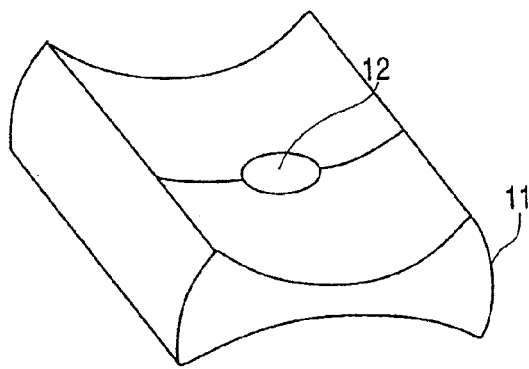
FIG. 23 is a side view, from slightly above, of a metal alloy or plastic coupling element used in the adjustable fastening arrangement of the invention for attaching the calf shank to the foot keel as shown in FIG. 3.
Figure 24:
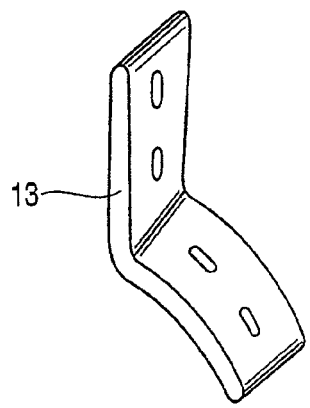
FIG. 24 is a view from the side and slightly to the front of a pylon adapter used on the prosthetic foot of FIGS. 3-5, and also useful with the foot of FIGS. 28 and 29, for connecting the foot to a pylon to be attached to an amputee's leg.

The amputee can, through practice, find a setting for each activity that meets his/her needs as these needs relate to horizontal and vertical linear velocities. A jumper and a basketball player, for example, need more vertical lift than a sprint runner. The coupling element 11 is a plastic or metal alloy alignment coupling (see FIGS. 3, 4 and 23) sandwiched between the attached foot keel 2 and calf shank 6. The releasable fastener 8 extends through a hole 12 in the coupling element. The coupling element extends along the attached portion of the calf shank and the proximate, posterior surface of the keel midfoot portion 5.

The curved lower end 7 of the calf shank 6 is in the shape of a parabola with the smallest radius of curvature of the parabola located at the lower end and extending upwardly, and initially anteriorly in the parabola shape. A posteriorly facing concavity is formed by the curvature of the calf shank as depicted in FIG. 3. The parabola shape is advantageous in that it has increased dynamic response characteristics in creating both improved horizontal linear velocity associated with the relatively larger radii proximal terminal end thereof, while having a smaller radius of curvature at its lower end for quicker response characteristics. The larger radii of curvature at the upper end of the parabola shape enable the tangential line A, explained with reference to FIGS. 1 and 2, to remain more vertically oriented with changes in alignment, which creates improved horizontal linear velocity.

The parabolic shaped calf shank responds to initial contact ground forces in human gait by compressing or coiling in on itself. This makes the radii of the parabola curve smaller, and as a consequence, the resistance to compression is decreased. In contrast, as the parabolic shaped calf shank responds to heel off ground reaction forces (GRFs) in human gait by expanding, this makes the radii of the parabola curve larger and as a consequence resistance is much greater than the aforementioned compressive resistance. These resistances are associated with the human's anterior and posterior calf muscle function in human gait. At initial contact to foot flat of human gait, the smaller anterior calf muscle group responds to GRFs by eccentrically contracting to lower the foot to the ground and a dorsiflexion moment is created. From foot flat to toe off the larger posterior calf muscle group responds to GRFs also by eccentrically contracting and a greater plantar flexion moment is created. This moment size relates to the calf anterior and posterior muscle group difference in size. As a consequence, the prosthetic calf shank's resistance to the dorsiflexion and plantar flexion moments in human gait are mimicked and normal gait is achieved. The parabolic curves variable resistance capability mimics the human calf musculature function in human gait and running and jumping activities, and as a consequence prosthetic efficiency is achieved.

A human being walks at approximately three miles per hour. A 4:00 minute miler runs at 12 miles per hour and a 10 second, 100 meter sprinter sprints at 21 miles per hour. This is a 1 to 4 to 7 ratio. The horizontal component of each task is greater as the velocity of the activity increases. As a consequence, the size of the prosthetic calf shank radii can be predetermined. A walker needs a smaller radii parabolic curved calf shank than a miler and a sprinter. A sprint runner needs a parabolic curved calf shank that is seven times as large. This relationship shows how to determine the parabolic radii for walkers, runners and sprinters. It is of significance because sprint runners have increased range of motion requirements and their calf shanks must be stronger to accept the increased loads associated with this activity. A wider or larger parabolic calf shank will be a relatively flatter curve, which equates to greater structural strength with increased range of motion.

A pylon adapter 13 is connected to the upper end of the calf shank 6 by fasteners 14. The adapter 13 in turn is secured to the lower end of pylon 15 by fasteners 16. Pylon 15 is secured to the lower limb of the amputee by a supporting structure (not shown) attached to the leg stump.

The forefoot, midfoot and hindfoot portions of the foot keel 2 are formed of a single piece of resilient material in the example embodiment. For example, a solid piece of material, plastic in nature, having shape-retaining characteristics when deflected by the ground reaction forces can be employed. More particularly, the foot keel and also the calf shank can be formed of laminated composite material having reinforcing fiber laminated with polymer matrix material. In particular, a high strength graphite, laminated with epoxy thermosetting resins, or extruded plastic utilized under the tradename of Delran, or degassed polyurethane copolymers, may be used to form the foot keel and also the calf shank. The functional qualities associated with these materials afford high strength with low weight and minimal creep. The thermosetting epoxy resins are laminated under vacuum utilizing prosthetic industry standards. The polyurethane copolymers can be poured into negative molds and the extruded plastic can be machined. Each material of use has its advantages and disadvantages. It has been found that the laminated composite material for the foot keel and the calf shank can also advantageously be a thermo-formed (prepreg) laminated composite material manufactured per industry standards, with reinforcing fiber and a thermoplastic polymer matrix material for superior mechanical expansion qualities. A suitable commercially available composite material of this kind is CYLON® made by Cytec Fiberite Inc. of Havre de Grace, Md. The calf shank and foot keel could also be resilient metal members formed, for example, of spring steel, stainless steel, titanium alloy, or other metal alloy.

The resilient material's physical properties as they relate to stiffness, flexibility and strength are all determined by the thickness of the material. A thinner material will deflect easier than a thicker material of the same density. The material utilized, as well as the physical properties, are associated with the stiffness to flexibility characteristics in the prosthetic foot keel and calf shank. The thickness of the foot keel and calf shank are uniform or symmetrical in the example embodiment of FIGS. 3-5, but the thickness along the length of these components can be varied as discussed below, such as by making the hindfoot and forefoot areas thinner and more responsive to deflection in the midfoot region.

To aid in providing the prosthetic foot 1 with a high low dynamic response capability, the midfoot portion 5 is formed by a longitudinal arch such that the medial aspect of the longitudinal arch has a relatively higher dynamic response capability than the lateral aspect of the longitudinal arch. For this purpose, in the example embodiment, the medial aspect of the longitudinal arch concavity is larger in radius than the lateral aspect thereof.

The interrelationship between the medial to lateral radii size of the longitudinal arch concavity of the midfoot portion 5 is further defined as the anterior posterior plantar surface weight bearing surface areas of the foot keel 2. The line $T_1$-$T_2$ on the anterior section of 5 in FIG. 8 represents the anterior plantar surface weight bearing area. Line $P_1$-$P_2$ represents the posterior plantar weight-bearing surface of 5. The plantar weight bearing surfaces on the lateral side of the foot would be represented by the distance between $T_1$-$P_1$. The plantar weight bearing surfaces on the medial side of the foot 2 are represented by the distance between $P_2$-$T_2$. The distances represented by $T_1$-$P_1$ and $P_2$-$T_2$ determine the radii size, and as a result the high low dynamic response interrelationship is determined and can be influenced by converging or diverging these two lines $T_1$-$T_2$ to $P_1$-$P_2$. As a result, high low dynamic response can be determined in structural design. The $T_1$-$T_2$ forefoot plantar weight bearing surface can be deviated as little as 5° from the normal to the longitudinal axis A-A of the foot keel to create this high low dynamic response, FIG. 8.

The posterior end 17 of the hindfoot portion 4 is shaped in an upwardly curved arch that reacts to ground reaction forces during heel strike by compressing for shock absorption. The heel formed by the hindfoot portion 4 is formed with a posterior lateral corner 18 which is more posterior and lateral than the medial corner 19 to encourage hindfoot eversion during initial contact phase of gait. The anterior end 20 of the forefoot portion 3 is shaped in an upwardly curved arch to simulate the human toes being dorsiflexed in the heel rise toe off position of the late stance phase of gait. Rubber or foam pads 63 and 64 are provided on the lower forefoot and hindfoot as cushions.

Improved biplanar motion capability of the prosthetic foot is created by medial and lateral expansion joint holes 21 and 22 extending through the forefoot portion 3 between dorsal and plantar surfaces thereof. Expansion joints 23 and 24 extend forward from respective ones of the holes to the anterior edge of the forefoot portion to form medial, middle and lateral expansion struts 25-27 which create improved biplanar motion capability of the forefoot portion of the foot keel. The expansion joint holes 21 and 22 are located along a line, B-B in FIG. 5, in the transverse plane which extends at an angle α of 35° to the longitudinal axis A-A of the foot keel with the medial expansion joint hole 21 more anterior than the lateral expansion joint hole 22.

The angle α of line B-B to longitudinal axis A-A in FIG. 5 can be as small as 5° and still derive a high low dynamic response. As this angle α changes, so should the angle Z of the line $T_1$-$T_2$ in FIG. 8. The expansion joint holes 21 and 22 as projected on a sagittal plane are inclined at an angle of 45° to the transverse plane with the dorsal aspect of the holes being more anterior than the plantar aspect. With this arrangement, the distance from the releasable fastener 8 to the lateral expansion joint hole 22 is shorter than the distance from the releasable fastener to the medial expansion joint hole 21 such that the lateral portion of the prosthetic foot 1 has a shorter toe lever than the medial for enabling midfoot high and low dynamic response. In addition, the distance from the releasable fastener 8 to the lateral plantar weight bearing surface as represented by $T_1$, line is shorter than the distance from the releasable fastener to the medial plantar surface weight bearing surface as represented by the line $T_2$—such that the lateral portion of the prosthetic foot 1 has a shorter toe lever than the medial for enabling midfoot high low dynamic response.

The anterior of the hindfoot portion 4 of the foot keel 2 further includes an expansion joint hole 28 extending through the hindfoot portion 4 between dorsal and plantar surfaces thereof. An expansion joint 29 extends posteriorly from the hole 28 to the posterior edge of the hindfoot portion to form expansion struts 30 and 31. These create improved biplanar motion capability of the hindfoot portion of the foot. As a variation, the expansion joint holes 28, 21 and 22 can each have another small hole, 28A, 21A and 22A, FIG. 8, drilled through the area adjacent the expansion joint to act as a stress relief hole. The additional small hole redirects the performing wave pattern and decreases tearing and/or breaking of the foot keel.

A dorsal aspect of the midfoot portion 5 and the forefoot portion 3 of the foot keel 2 form the upwardly facing concavity, 32 in FIG. 3, so that it mimics in function the fifth ray axis of motion of a human foot. That is, the concavity 32 has a longitudinal axis C-C which is oriented at an angle $\beta$ of 5° to 35° to the longitudinal axis A-A of the foot keel with the medial being more anterior than the lateral to encourage fifth ray motion in gait as in the oblique low gear axis of rotation of the second to fifth metatarsals in the human foot.

The importance of biplanar motion capability can be appreciated when an amputee walks on uneven terrain or when the athlete cuts medially or laterally on the foot. The direction of the ground force vector changes from being sagittally oriented to having a frontal plane component. The ground will push medially in opposite direction to the foot pushing laterally. As a consequence to this, the calf shank leans medially and weight is applied to the medial structure of the foot keel. In response to these pressures, the medial expansion joint struts 25 and 31 of the foot keel 2 dorsiflex (deflect upward) and invert, and the lateral expansion joint struts 27 and 30 plantar flex (deflect downwards) and evert. This motion tries to put the plantar surface of the foot flat on the ground (plantar grade).

Figure 6:
FIG. 6 is a side view of another foot keel of the invention, especially for sprinting, which may be used in the prosthetic foot of the invention.
Figure 7:
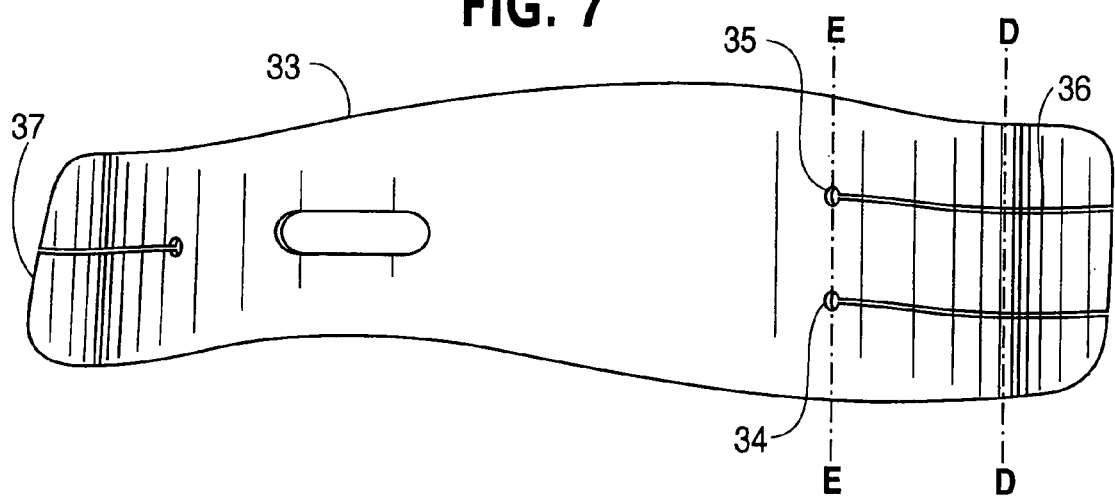
FIG. 7 is a top view of the foot keel of FIG. 6.

Another foot keel 33 of the invention, especially for sprinting, may be used in the prosthetic foot of the invention, see FIGS. 6 and 7. The body's center of gravity in a sprint becomes almost exclusively sagittal plane oriented. The prosthetic foot does not need to have a low dynamic response characteristic. As a consequence, the 5° to 35° external rotation orientation of the longitudinal axis of the forefoot, midfoot concavity as in foot keel 2 is not needed. Rather, the concavity's longitudinal axis D-D orientation should become parallel to the frontal plane as depicted in FIGS. 6 and 7. This makes the sprint foot respond in a sagittal direction only. Further, the orientation of the expansion joint holes 34 and 35 in the forefoot and midfoot portions, along line E-E, is parallel to the frontal plane, i.e., the lateral hole 35 is moved anteriorly and in line with the medial hole 34 and parallel to the frontal plane. The anterior terminal end 36 of the foot keel 33 is also made parallel to the frontal plane. The posterior terminal heel area 37 of the foot keel is also parallel to the frontal plane. These modifications effect in a negative way the multi-use capabilities of the prosthetic foot. However, its performance characteristics become task specific. Another variation in the sprint foot keel 33 is in the toe, ray region of the forefoot portion of the foot where 15° of dorsiflexion in the foot keel 2 are increased to 25-40° of dorsiflexion in foot keel 33.

Figure 9:
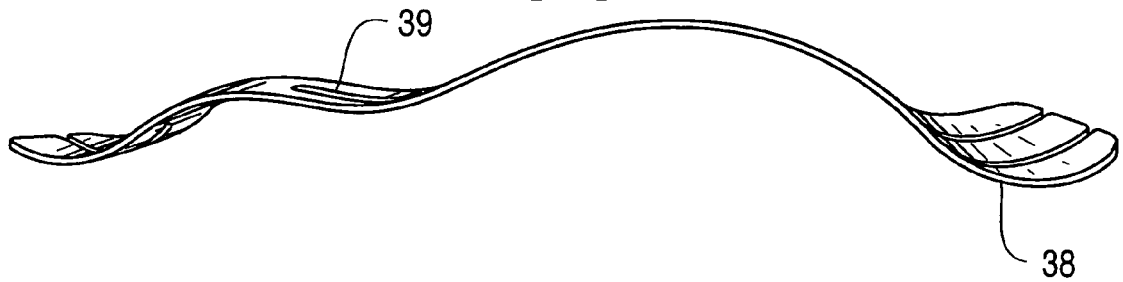
FIG. 9 is a side view of an additional foot keel of the invention for the prosthetic foot particularly useful for sprinting by an amputee that has had a Symes amputation of the foot.
Figure 10:
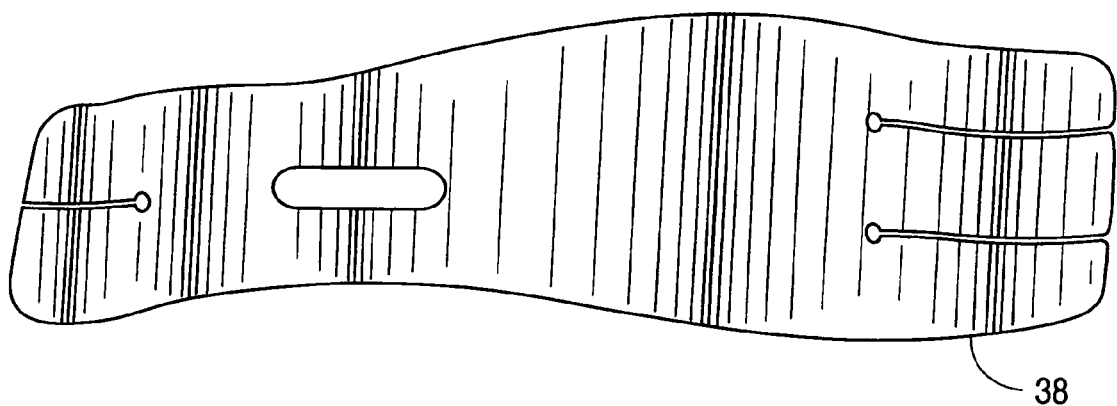
FIG. 10 is a top view of the foot keel of FIG. 9.
Figure 11:
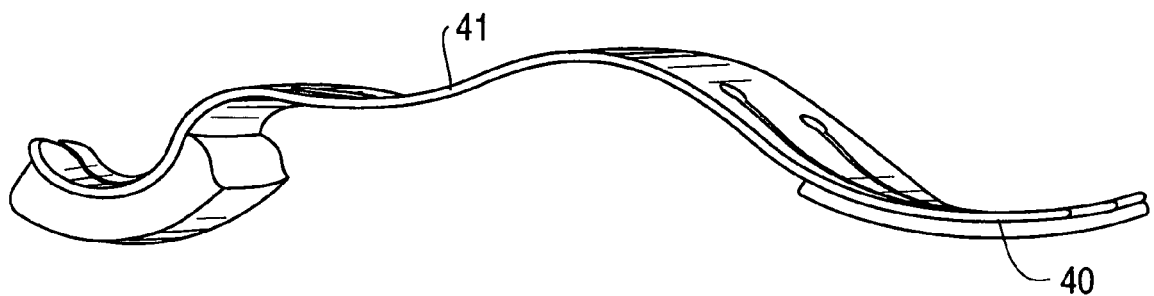
FIG. 11 is a further variation of foot keel for the prosthetic foot of the invention for a Symes amputee, the foot keel providing the prosthetic foot with high low dynamic response characteristics as well as biplanar motion capabilities.
Figure 12:
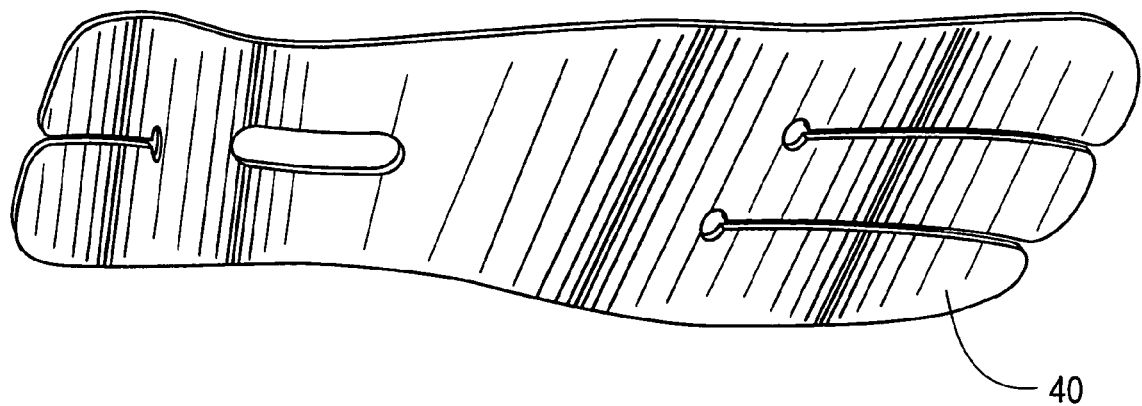
FIG. 12 is a top view of the foot keel of FIG. 11.

FIGS. 9 and 10 show an additional foot keel 38 of the invention for the prosthetic foot particularly useful for sprinting by an amputee that has had a Symes amputation of the foot. For this purpose, the midfoot portion of the foot keel 38 includes a posterior, upwardly facing concavity 39 in which the curved lower end of the calf shank is attached to the foot keel by way of the releasable fastener. This foot keel can be utilized by all lower extremity amputees. The foot keel 38 accommodates the longer residual limb associated with the Symes level amputee. Its performance characteristics are distinctively quicker in dynamic response capabilities. Its use is not specific to this level of amputation. It can be utilized on all transtibial and transfemoral amputations. The foot keel 40 in the example embodiment of FIGS. 11 and 12 also has a concavity 41 for a Symes amputee, the foot keel providing the prosthetic foot with high low dynamic response characteristic as well as biplanar motion capabilities like those of the example embodiment in FIGS. 3-5 and 8.

The functional characteristics of the several foot keels for the prosthetic foot 1 are associated with the shape and design features as they relate to concavities, convexities, radii size, expansion, compression, and material physical properties—all of these properties relating, to reacting to, ground forces in walking, running and jumping activities.

Figure 13:
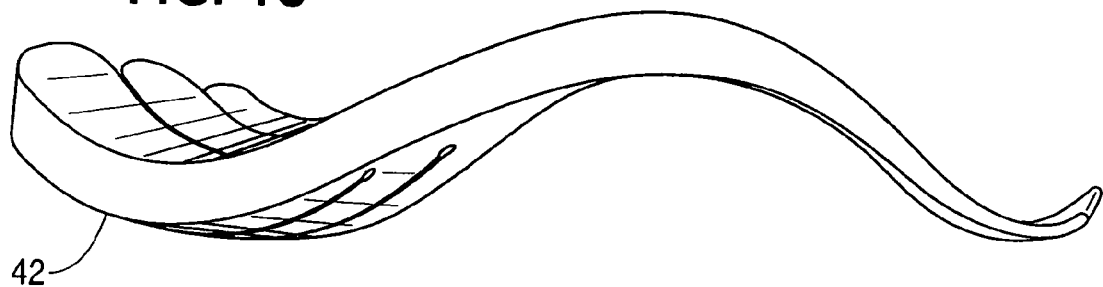
FIG. 13 is a side view of a foot keel of the invention wherein the thickness of the keel tapers, e.g., is progressively reduced, from the midfoot portion to the hindfoot portion of the keel.
Figure 14:
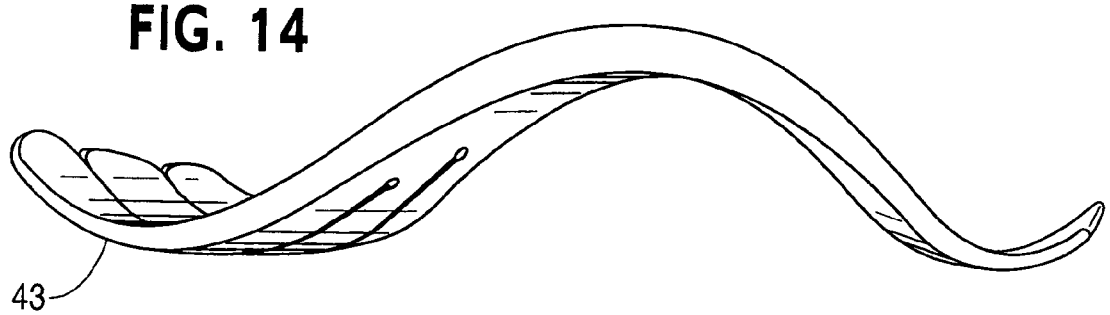
FIG. 14 is a side view of another form of the foot keel wherein the thickness tapers from the midfoot toward both the forefoot and hindfoot of the keel.
Figure 16:
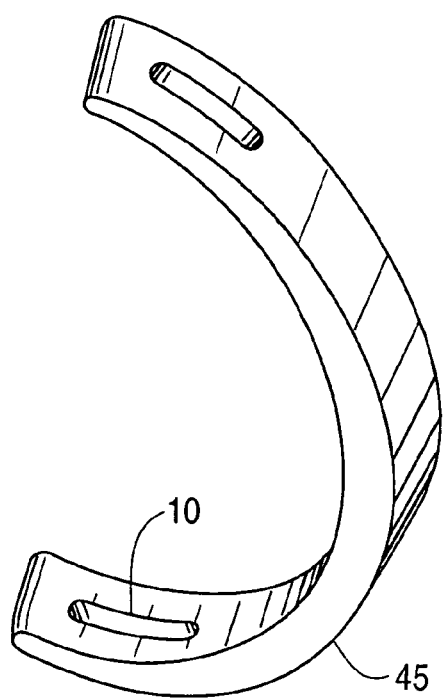
FIG. 16 is a side view like FIG. 15 but showing another calf shank tapered from the middle towards both its upper and lower ends.
Figure 17:
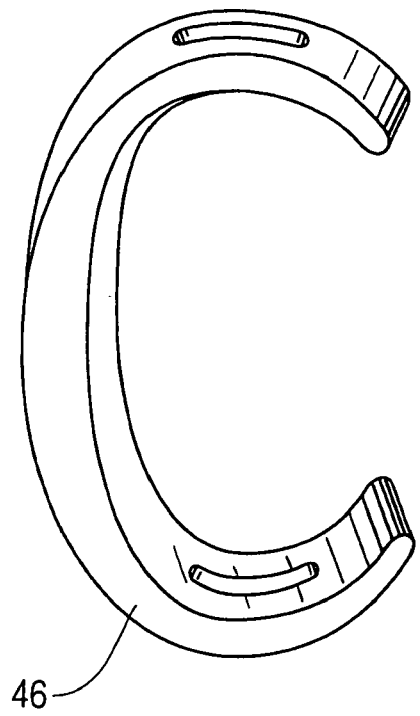
FIG. 17 is a side view of a C-shaped calf shank for the prosthetic foot, the calf shank thickness tapering from the middle towards both its upper and lower ends.
Figure 18:
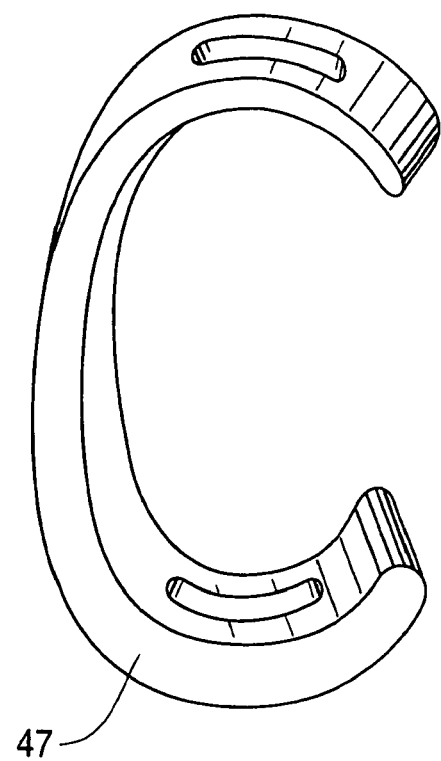
FIG. 18, is a side view of another example of a C-shaped calf shank for the prosthetic foot, the thickness of the calf shank being progressively reduced from its midportion to its upper end.
Figure 19:
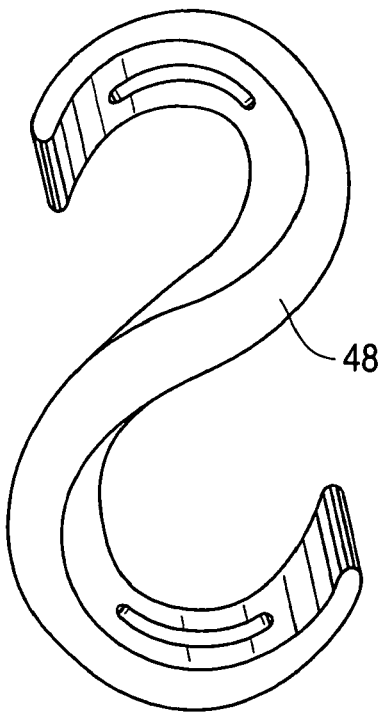
FIG. 19 is a side view of an S-shaped calf shank for the prosthetic foot, both ends being progressively reduced in thickness from the middle thereof.
Figure 20:
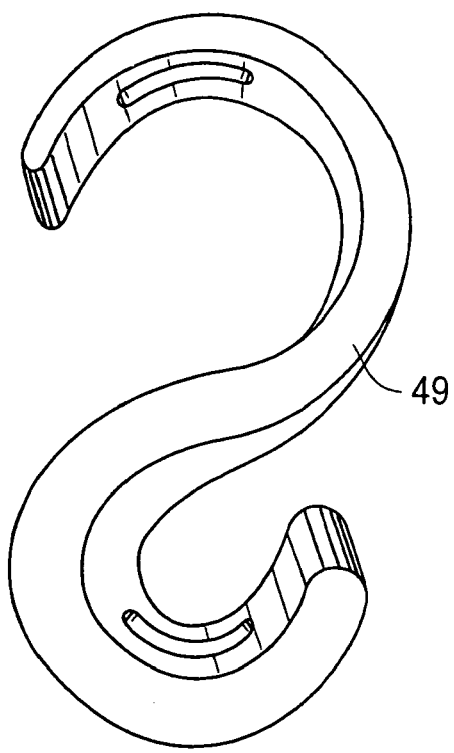
FIG. 20 is a further example of an S-shaped calf shank which is tapered in thickness only at its upper end.
Figure 21:
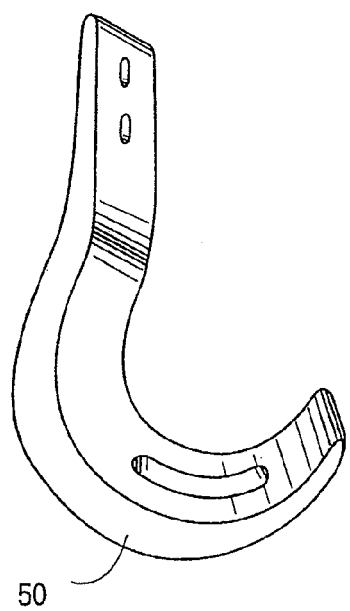
FIG. 21 is a side view of a J-shaped calf shank, tapered at each end, for the prosthetic foot of the invention.
Figure 22:
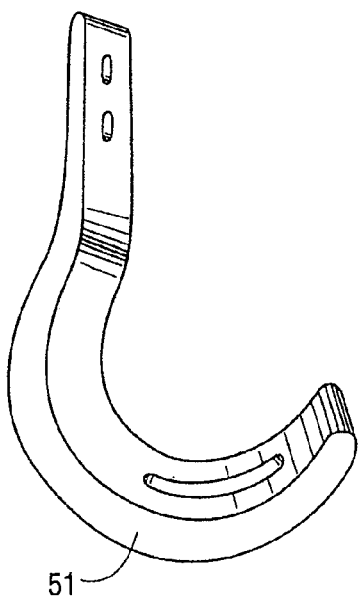
FIG. 22 is a view like FIG. 21 but showing a J-shaped calf shank which is progressively reduced in thickness towards only its upper end.

The foot keel 42 in FIG. 13 is like that in the example embodiment of FIGS. 3-5 and 8, except that the thickness of the foot keel is tapered from the midfoot portion to the posterior of the hindfoot. The foot keel 43 in FIG. 14 has its thickness progressively reduced or tapered at both its anterior and posterior ends. Similar variations in thickness are shown in the calf shank 44 of FIG. 15 and the calf shank 45 of FIG. 16 which may be used in the prosthetic foot 1. Each design of the foot keel and calf shank create different functional outcomes, as these function outcomes relate to the horizontal and vertical linear velocities which are specific to improving performance in varied athletic related tasks. The capability of multiple calf shank configurations and adjustments in settings between the foot keel and the calf shank create a prosthetic foot calf shank relationship that allows the amputee and/or the prosthetist the ability to tune the prosthetic foot for maximum performance in a selected one of a wide variety of sport and recreational activities.

Other calf shanks for the prosthetic foot 1 are illustrated in FIGS. 17-22 and include C-shaped calf shanks 46 and 47, S-shaped calf shanks 48 and 49 and J-shaped calf shanks 50 and 51. The upper end of the calf shank could also have a straight vertical end with a pyramid attachment plate attached to this proximal terminal end. A male pyramid could be bolted to and through this vertical end of the calf shank as shown in FIGS. 28-30 and 33-36. Another embodiment of shank proximal attachment can be the anterior and/or posterior aspect of the amputee's socket and/or other prosthetic components. Plastic or aluminum fillers to accept the proximal male pyramid and the distal foot keel could also be provided in the elongated openings at the proximal and distal ends of the calf shank. The prosthetic foot of the invention is a modular system preferably constructed with standardized units or dimensions for flexibility and variety in use. An example of a pyramid attachment plate attached to the proximal terminal end of the calf shank is shown at 88 in the embodiment of FIG. 28.

All track related running activities take place in a counter-clockwise direction. Another, optional feature of the invention takes into account the forces acting on the foot advanced along such a curved path. Centripetal acceleration acts toward the center of rotation where an object moves along a curved path. Newton's third law is applied for energy action. There is an equal and opposite reaction. Thus, for every "center seeking" force, there is a "center fleeing" force. The centripetal force acts toward the center of rotation and the centrifugal force, the reaction force, acts away from the center of rotation. If an athlete is running around the curve on the track, the centripetal force pulls the runner toward the center of the curve while the centrifugal force pulls away from the center of the curve. To counteract the centrifugal force which tries to lean the runner outward, the runner leans inward. If the direction of rotation of the runner on the track is always counter-clockwise, then the left side is the inside of the track. As a consequence, according to a feature of the present invention, the left side of the right and left prosthetic foot calf shanks can be made thinner than the right side and the amputee runner's curve performance could be improved.

The foot keels 2, 33, 38, 42 and 43 in the several embodiments, are each 29 cm long with the proportions of the shoe 1 shown to scale in FIGS. 3, 4 and 5, and in the several views of the different calf shanks and foot keels. However, as will be readily understood by the skilled artisan, the specific dimensions of the prosthetic foot can be varied depending on the size, weight and other characteristics of the amputee being fitted with the foot. The length of the calf shank and its modulus of resiliency create its potential and capacity to store elastic energy. This elastic stored energy is transformed through the mechanical structure into a kinetic power which becomes a vectoral force with direction and magnitude qualities. Therefore, the longer the shank length the more the propulsive force. The shank proximal attachment point for the highest performing athletes should be kept as proximal as prosthetic components will allow.

The operation of the prosthetic foot 1 in walking and running stance phase gait cycles will now be considered. Newton's three laws of motion, that relate to law of inertia, acceleration and action-reaction, are the basis for movement kinematics in the foot 2. From Newton's third law, the law of action-reaction, it is known that the ground pushes on the foot in a direction equal and opposite to the direction the foot pushes on the ground. These are known as ground reaction forces. Many scientific studies have been done on human gait, running and jumping activities. Force plate studies show us that Newton's third law occurs in gait. From these studies, we know the direction the ground pushes on the foot.

The stance phase of walking/running activities can be further broken down into deceleration and acceleration phases. When the prosthetic foot touches the ground, the foot pushes anteriorly on the ground and the ground pushes back in an equal and opposite direction—that is to say the ground pushes posteriorly on the prosthetic foot. This force makes the prosthetic foot move. The stance phase analysis of walking and running activities begins with the contact point being the posterior lateral corner 18, FIGS. 5 and 8, which is offset more posteriorly and laterally than the medial side of the foot. This offset at initial contact causes the foot to evert and the calf shank to plantar flex. The calf shank always seeks a position that transfers the body weight through its shank, e.g., it tends to have its long vertical member in a position to oppose the ground forces. This is why it moves posteriorly-plantar flexes to oppose the ground reaction force which is pushing posteriorly on the foot.

The ground forces cause calf shanks 44, 45, 46, 47, 50 and 51 to compress with the proximal end moving posterior. With calf shanks 48, 49 the distal ½ of the calf shank would compress depending on the distal concavities orientation. If the distal concavity compressed in response to the GRF's the proximal concavity would expand and the entire calf shank unit would move posteriorally. The ground forces cause the calf shank to compress with the proximal end moving posteriorly. The calf shank lower tight radius compresses simulating human ankle joint plantar flexion and the forefoot is lowered by compression to the ground. At the same time to the posterior aspect of keel, as represented by hindfoot 4, depicted by 17 compresses upward through compression. Both of these compressive forces act as shock absorbers. This shock absorption is further enhanced by the offset posterior lateral heel 18 which causes the foot to evert, which also acts as a shock absorber, once the calf shank has stopped moving into plantar flexion and with the ground pushing posteriorly on the foot.

The compressed members of the foot keel and calf shank then start to unload—that is they seek their original shape and the stored energy is released—which causes the calf shank proximal end to move anteriorly in an accelerated manner. As the calf shank approaches its vertical starting position, the ground forces change from pushing posteriorly to pushing vertically upward against the foot. Since the prosthetic foot has posterior and anterior plantar surface weight bearing areas and these areas are connected by a non-weight bearing long arch shaped midportion, the vertically directed forces from the prosthesis cause the long arch shaped midportion to load by expansion. The posterior and anterior weight-bearing surfaces diverge. These vertically directed forces are being stored in the long arch midportion of the foot—as the ground forces move from being vertical in nature to anteriorly directed. The calf shank expands—simulating ankle dorsiflexion. This causes the prosthetic foot to pivot off of the anterior plantar weight-bearing surface. As weight unloading occurs, the longitudinal arch of the midfoot portion 5 and the expanded shank change from being expanded and seek their original shape which creates simulated plantar flexor muscle group movement patterns and outcomes. As a consequence the mechanical prosthetic structures release the elastic stored energy into kinetic power.

The long arch of the foot keel and the calf shank resist expansion of their respective structures. As a consequence, the calf shank anterior progression is arrested and the foot starts to pivot off the anterior plantar surface weight-bearing area. The expansion of the midfoot portion of the foot keel has as high and low response capability in the case of the foot keels in the example embodiments of FIGS. 3-5 and 8, FIGS. 11 and 12, FIG. 13 and FIG. 14. Since the midfoot forefoot transitional area of these foot keels is deviated 15° to 35° externally from the long axis of the foot, the medial long arch is longer than the lateral long arch. This is important because in the normal foot, during acceleration or deceleration, the medial aspect of the foot is used.

The prosthetic foot longer medial arch has greater dynamic response characteristic than the lateral. The lateral shorter toe lever is utilized when walking or running at slower speeds. The body's center of gravity moves through space in a sinusoidal curve. It moves medial, lateral, proximal and distal. When walking or running at slower speeds, the body's center of gravity moves more medial and lateral than when walking or running fast. In addition, momentum or inertia is less and the ability to overcome a higher dynamic response capability is less. The prosthetic foot of the invention is adapted to accommodate these principles in applied mechanics.

In addition, in the human gait cycle at midstance the body's center of gravity is as far lateral as it will go. From midstance through toe off the body's center of gravity (BCG) moves from lateral to medial. As a consequence, the body's center of gravity progresses over the lateral side of the foot keel 2. First (low gear) and as the BCG progresses forward, it moves medially on foot keel 2 (high gear). As a consequence, the prosthetic foot keel 2 has an automatic transmission effect. That is to say, it starts in low gear and moves into high gear every step the amputee takes.

As the ground forces push anteriorly on the prosthetic foot which is pushing posteriorly on the ground, as the heel begins to rise the anterior portion of the long arch of the midfoot portion is contoured to apply these posteriorly directed forces perpendicular to its plantar surface. This is the most effective and efficient way to apply these forces. The same can be said about the posterior hindfoot portion of the prosthetic foot. It is also shaped so that the posteriorly directed ground forces at initial contact are opposed with the foot keel's plantar surface being perpendicular to their applied force direction.

In the later stages of heel rise, toe off walking and running activities, the ray region of the forefoot portion is dorsiflexed 15°-35°. This upwardly extending arc allows the anteriorly directed ground forces to compress this region of the foot. This compression is less resisted than expansion and a smooth transition occurs to the swing phase of gait and running with the prosthetic foot. In later stages of stance phase of gait, the expanded calf shank and the expanded midfoot long arch release their stored energy adding to the forward and upward propulsion of the trailing limb and amputee's body center of gravity.

One of the main propulsion mechanisms in human gait is called the active propulsion phase. As the heel lifts, the body weight is now forward of the support limb and the center of gravity is falling. As the body weight drops over the forefoot rocker FIG. 5, line C-C there is a downward acceleration, which results in the highest vertical force received by the body. Acceleration of the leg forward of the ankle, associated with lifting of the heel, results in a posterior shear against the ground. As the center of pressure moves anterior to the metatarsal heads axis of rotation the effect is an ever-increasing dorsiflexion torque. This creates a full forward fall situation that generates the major progression force used in walking. The signs of effective ankle function during the active propulsion are heel lift, minimal joint motion, and a nearly neutral ankle position. A stable midfoot is essential for normal sequencing in heel lift.

The posterior aspect of the hindfoot and the forefoot region of the foot keel incorporate expansion joint holes and expansion joint struts in several of the embodiments as noted previously. The orientation of the expansion joint holes act as a mitered hinge and biplanar motion capabilities are improved for improving the total contact characteristics of the plantar surface of the foot when walking on uneven terrain.

The Symes foot keels in FIGS. 9-12 are distinctively different in dynamic response capabilities—as these capabilities are associated with walking, running and jumping activities. These foot keels differ in four distinct features. These include the presence of a concavity in the proximate, posterior of the midfoot portion for accommodating the Symes distal residual limb shape better than a flat surface. This concavity also lowers the height of the foot keel which accommodates the longer residual limb that is associated with the Symes level amputee. The alignment concavity requires that the corresponding anterior and posterior radii of the arched foot keel midportion be more aggressive and smaller in size. As a consequence, all of the midfoot long arch radii and the hindfoot radii are tighter and smaller. This significantly affects the dynamic response characteristics. The smaller radii create less potential for a dynamic response. However, the prosthetic foot responds quicker to all of the aforementioned walking, running and jumping ground forces. The result is a quicker foot with less dynamic response.

Improved task specific athletic performance can be achieved with alignment changes using the prosthetic foot of the invention, as these alignment changes affect the vertical and horizontal components of each task. The human foot is a multi-functional unit—it walks, runs and jumps. The human tibia fibula calf shank structure on the other hand is not a multi-functional unit. It is a simple lever which applies its forces in walking, running and jumping activities parallel to its long proximal-distal orientation. It is a non-compressible structure and it has no potential to store energy. On the other hand, the prosthetic foot of the invention has dynamic response capabilities, as these dynamic response capabilities are associated with the horizontal and vertical linear velocity components of athletic walking, running and jumping activities and out-performing the human tibia and fibula. As a consequence, the possibility exists to improve amputee athletic performance. For this purpose, according to the present invention, the fastener 8 is loosened and the alignment of the calf shank and the foot keel with respect to one another is adjusted in the longitudinal direction of the foot keel. Such a change is shown in connection with FIGS. 1 and 2. The calf shank is then secured to the foot keel in the adjusted position with the fastener 8. During this adjustment, the bolt of the fastener 8 slides relative to one or both of the opposed, relatively longer, longitudinally extending openings 9 and 10 in the foot keel and calf shank, respectively.

An alignment change that improves the performance characteristic of a runner who makes initial contact with the ground with the foot flat as in a midfoot strike runner, for example, is one wherein the foot keel is slid anterior relative to the calf shank and the foot plantar flexed on the calf shank. This new relationship improves the horizontal component of running. That is, with the calf shank plantar flexed to the foot, and the foot making contact with the ground in a foot flat position as opposed to initially heel contact, the ground immediately pushes posteriorly on the foot that is pushing anteriorly on the ground. This causes the calf shank to move rapidly forward (by expanding) and downwardly. Dynamic response forces are created by expansion which resists the calf shank's direction of initial movement. As a consequence, the foot pivots over the metatarsal plantar surface weight-bearing area. This causes the midfoot region of the keel to expand which is resisted more than compression. The net effect of the calf shank expansion and the midfoot expansion is that further anterior progression of the calf shank is resisted which allows the knee extenders and hip extenders in the user's body to move the body's center of gravity forward and proximal in a more efficient manner (i.e., improved horizontal velocity). In this case, more forward than up than in the case of a heel toe runner whose calf shank's forward progression is less resisted by the calf shank starting more dorsiflexed (vertical) than a foot flat runner.

To analyze the sprint foot in function, an alignment change of the calf shank and foot keel is made. Advantage is taken of the foot keel having all of its concavities with their longitudinal axis orientation parallel to the frontal plane. The calf shank is plantar flexed and slid posterior on the foot keel. This lowers the distal circles even further than on the flat foot runner with the multi-use foot keel like that in FIGS. 3-5 and 8, for example. As a consequence, there is even greater horizontal motion potential and the dynamic response is directed into this improved horizontal capability.

The sprinters have increased range of motion, forces and momentum (inertia)—momentum being a prime mover. Since their stance phase deceleration phase is shorter than their acceleration phase, increased horizontal linear velocities are achieved. This means that at initial contact, when the toe touches the ground, the ground pushes posteriorly on the foot and the foot pushes anteriorly on the ground. The calf shank which has increased forces and momentum is forced into even greater flexion and downward movement than the initial contact foot flat runner. As a consequence to these forces, the foot's long arch concavity is loaded by expansion and the calf shank is loaded by expansion. These expansion forces are resisted to a greater extent than all the other previously mentioned forces associated with running. As a consequence, the dynamic response capability of the foot is proportional to the force applied. The human tibia fibula calf shank response is only associated with the energy force potential—it is a straight structure and it cannot store energy. These expansion forces in the prosthetic foot of the invention in sprinting are greater in magnitude than all the other previously mentioned forces associated with walking and running. As a consequence, the dynamic response capability of the foot is proportional to the applied forces and increased amputee athletic performance, as compared with human body function, is possible.

Figure 25:
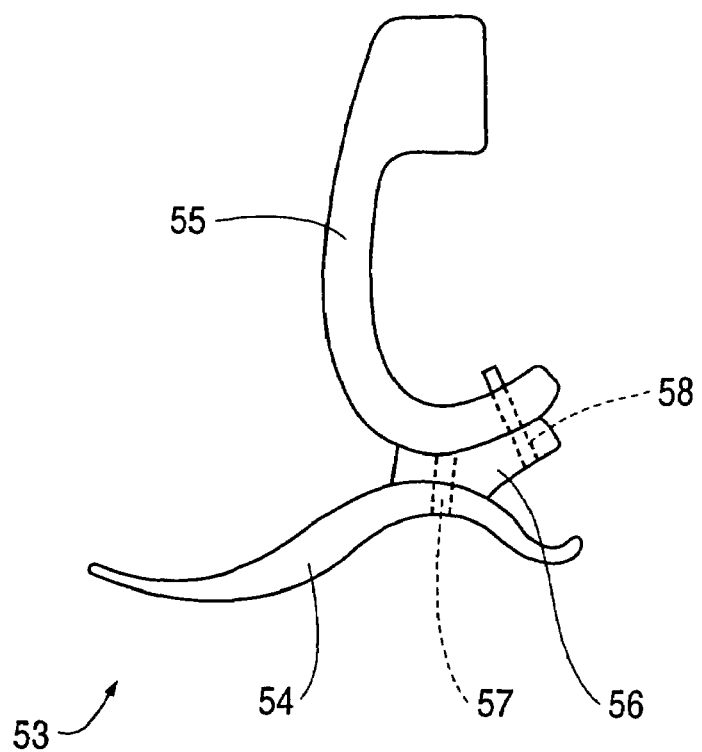
FIG. 25 is a side view of another prosthetic foot of the invention similar to that in FIG. 3, but showing use of a coupling element with two releasable fasteners spaced longitudinally connecting the element to the calf shank and foot keel, respectively.
Figure 26:
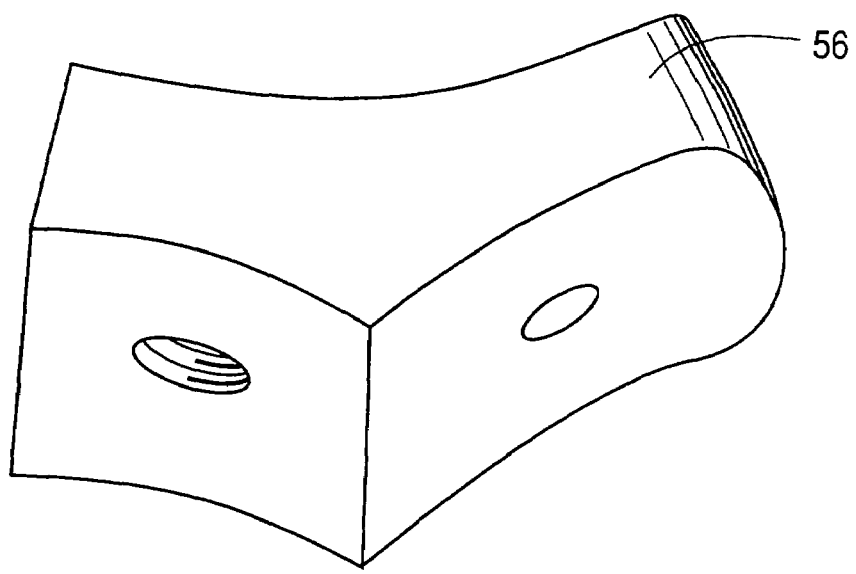
FIG. 26 is an enlarged side view of the coupling element in FIG. 25.
Figure 27:
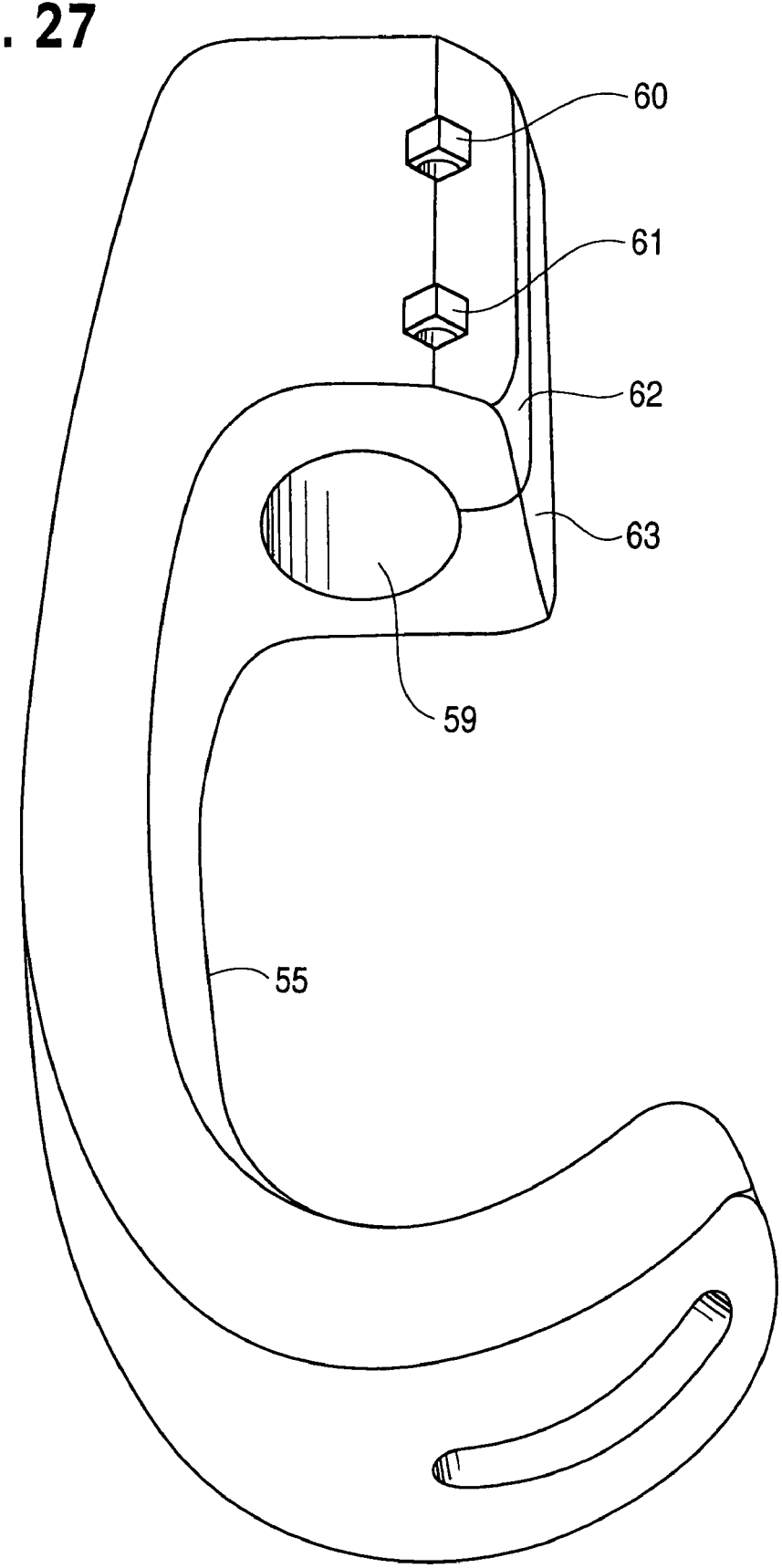
FIG. 27 is an enlarged side view of the calf shank of the prosthetic foot of FIG. 25.

The prosthetic foot 53 depicted in FIG. 25 is like that in FIG. 3 except for the adjustable fastening arrangement between the calf shank and the foot keel and the construction of the upper end of the calf shank for connection to the lower end of a pylon. In this example embodiment, the foot keel 54 is adjustably connected to the calf shank 55 by way of plastic or metal alloy coupling element 56. The coupling element is attached to the foot keel and calf shank by respective releasable fasteners 57 and 58 which are spaced from one another in the coupling element in a direction along the longitudinal direction of the foot keel. The fastener 58 joining the coupling element to the calf shank is more posterior than the fastener 57 joining the foot keel and the coupling element. By increasing the active length of the calf shank in this way, the dynamic response capabilities of the calf shank itself are increased. Changes in alignment are made in cooperation with longitudinally extending openings in the calf shank and foot keel as in other example embodiments.

The upper end of the calf shank 55 is formed with an elongated opening 59 for receiving a pylon 15. Once received in the opening, the pylon can be securely clamped to the calf shank by tightening bolts 60 and 61 to draw the free side edges 62 and 63 of the calf shank along the opening together. This pylon connection can be readily adjusted by loosening the bolts, telescoping the pylon relative to the calf shank to the desired position and reclamping the pylon in the adjusted position by tightening the bolts.

The prosthetic foot 70 shown in FIGS. 28-32 is similar to those in FIGS. 3-5, 8, 23 and 24 and FIGS. 25-27, but further includes a calf shank range of motion limiter and dampener device 71 on the foot to limit the extent of the motion of the upper end of the calf shank with force loading and unloading of the calf shank during use of the foot by the amputee. This feature is especially useful in a prosthetic foot having a relatively long calf shank where the wearer is to engage in activities such as running and jumping that generate forces in the calf shank many times the wearer's body weight, e.g., with running 5-7 times body weight and jumping 11-13 times body weight. In contrast, the forces generated in walking are only 1-1½ times body weight.

The device 71 in the example embodiment is a two-way acting piston cylinder unit in which pressurized fluids, a gas such as air or a hydraulic liquid, are provided through respective fittings 73 and 74. The device has two variable controls, one for compression, one for expansion, which permit adjustment of the permissible extent of the motion of the upper end of the calf shank 72 in both compression and expansion of the calf shank in force loading and unloading. The device 71 also dampens the energy being stored or released during calf shank compression and expansion. The opposite ends of the piston-cylinder device 71 are connected to the upper end of the calf shank and the lower portion of the foot, and preferably in the example embodiment to respective ends of the calf shank at pivot connections 75 and 76 which are preferably ball joints.

Figure 31:
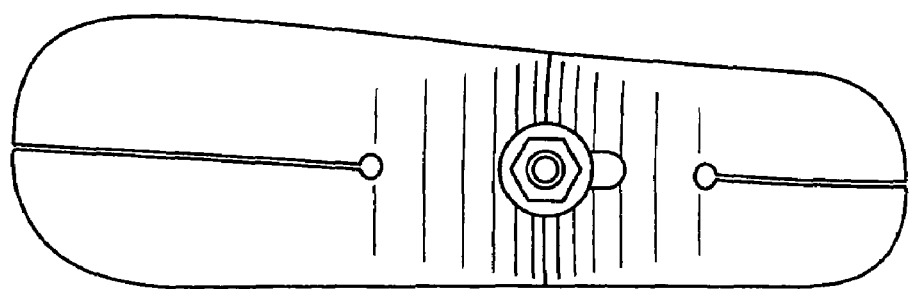
FIG. 31 is a bottom view of the prosthetic foot of FIG. 28.
Figure 32:
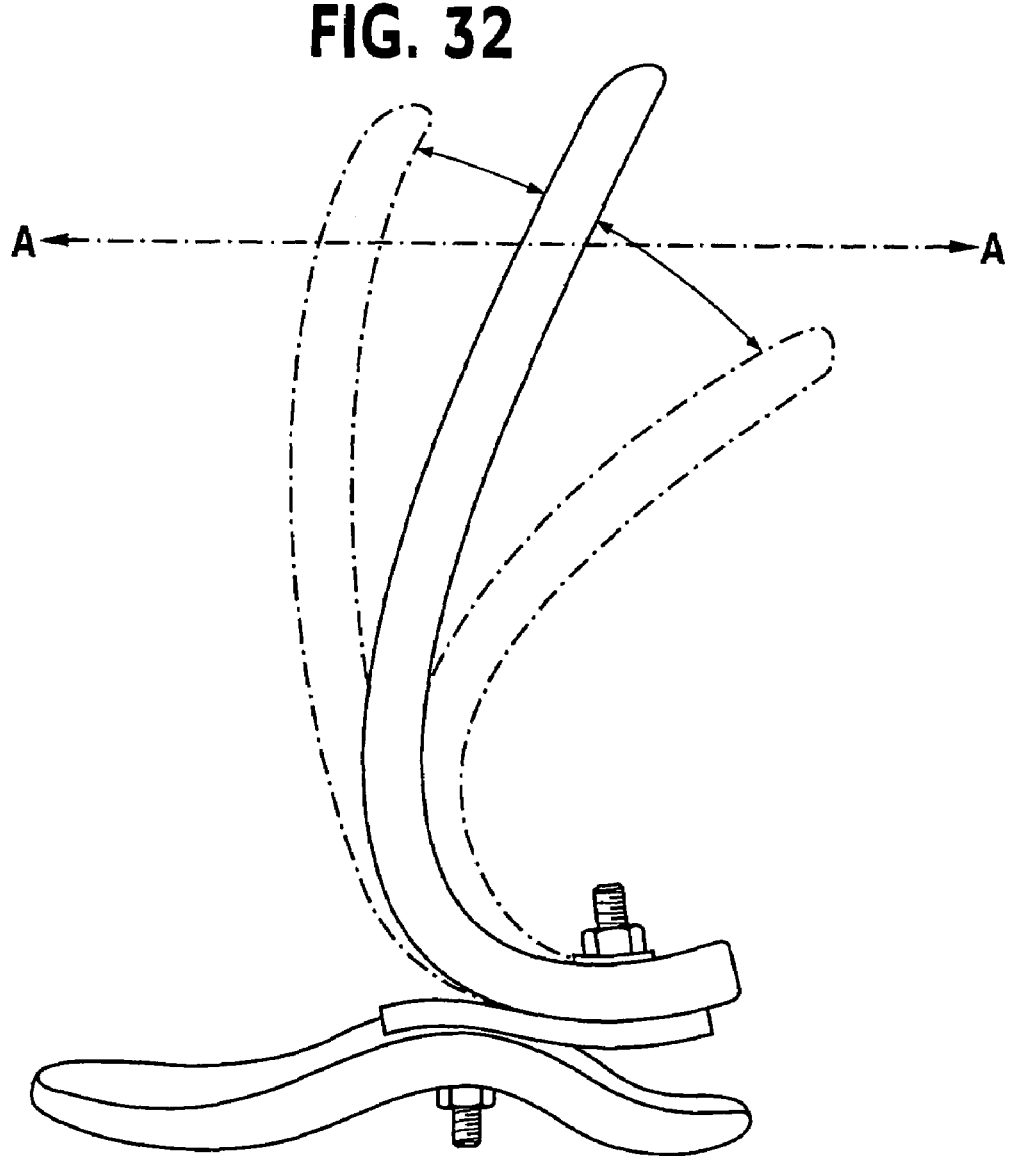
FIG. 32 is a side view of the calf shank and foot keel of the prosthetic foot of FIG. 28 illustrating an example of the motion of the upper end of the calf shank resulting from force loading and unloading the calf shank during use of the prosthetic foot.

The motion of the upper end of the calf shank 72 of the foot 70 in compression and expansion of the calf shank is depicted in FIG. 32. The generally parabola shape of the calf shank is such that the upper end of the calf shank can move longitudinally with respect to the foot keel 77 and lower end of the calf shank connected thereto, e.g., along direction A-A in FIGS. 5 and 32, with compression and expansion of the calf shank in force loading and unloading thereof. Thus, the improved dynamic response capabilities of the prosthetic foot are retained in the example embodiment of FIGS. 28-32.

The device 71 is not limited to the described piston cylinder unit but could be another velocity control and/or motion limiting device. For example, it is envisioned that the posterior range of motion limiting dampening device 71 employed on the calf shank of the prosthetic foot could be a microprocessor-controlled hydraulic unit with compression and expansion phase control, such as those now used for controlling motion in artificial knee joints. In such case, on-board sensors are provided that read and adapt to the individual's movements. By using special software and a PC, fine adjustments can be made to tailor the microprocessor controlled hydraulic unit to the amputee. Moments can be measured as much as 50 times per second—ensuring the dynamic gait is as similar to natural walking as possible. Because of the responsiveness of the hydraulic unit, it is suitable for a broad spectrum of lower limb amputees. A lithium-ion battery loaded in the unit provides enough energy to operate the hydraulic unit for a full day. The resistance for compression is adjusted independent of the expansion adjustments. Multiple integrated sensors stream gait analysis data to the on-board microprocessor that automatically adjusts the stance and swing phase characteristics of the unit 50 times per second.

This microprocessor controlled hydraulic unit of device 71 is more responsive than a mechanical hydraulic unit. An electrically controlled compression (plantar flexion) valve, adjusts 50 times per second. The compression valve in the unit is automatically fully opened during pre-swing. As a result, the unit is extremely easy to compress flex at slow speeds, in confined areas, and under similar conditions. The speed of the servo motor of the unit allows it to close the compression (plantar flexion) and expansion dorsiflexion valves very rapidly, in response to the microprocessor commands sent 50 times per second. When the valves are nearly closed, the unit dampening force becomes very high, making rapid walking and even running possible. The unique prosthetist-adjustable dynamic factor allows the hydraulic unit to be optimized for all gait patterns from slow to aggressive, fast gait speeds and movements. This ability to "tune" a microprocessor controlled hydraulic unit to the individual's unique gait pattern enables a wide range of cadences to be obtained in the prosthetic foot with high gait efficiency and comfort. That is, the use of a microprocessor hydraulic unit as the device 71 enhances the variable cadence required when the prosthetic foot is utilized by active amputees.

Figure 29:
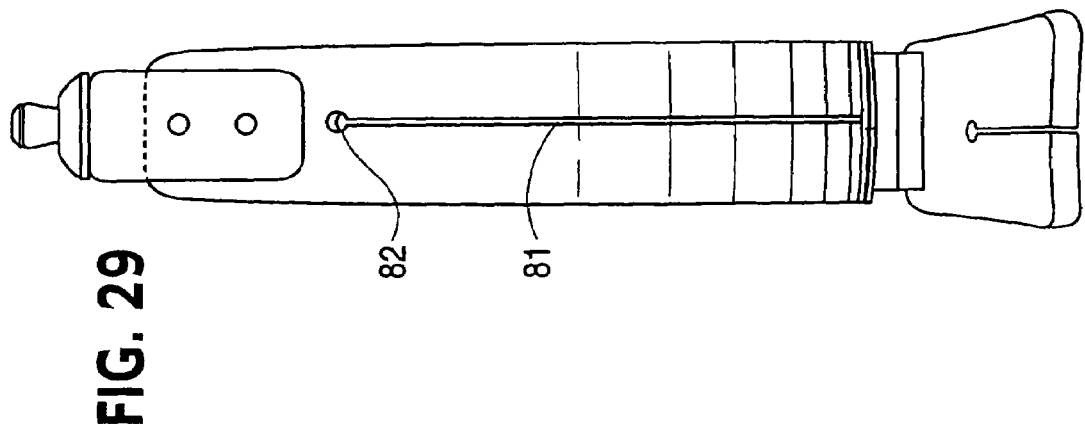
FIG. 29 is a front view of the prosthetic foot as seen from the left side of the prosthetic foot depicted in FIG. 28 showing a longitudinal slot in the calf shank of the foot.
Figure 28:
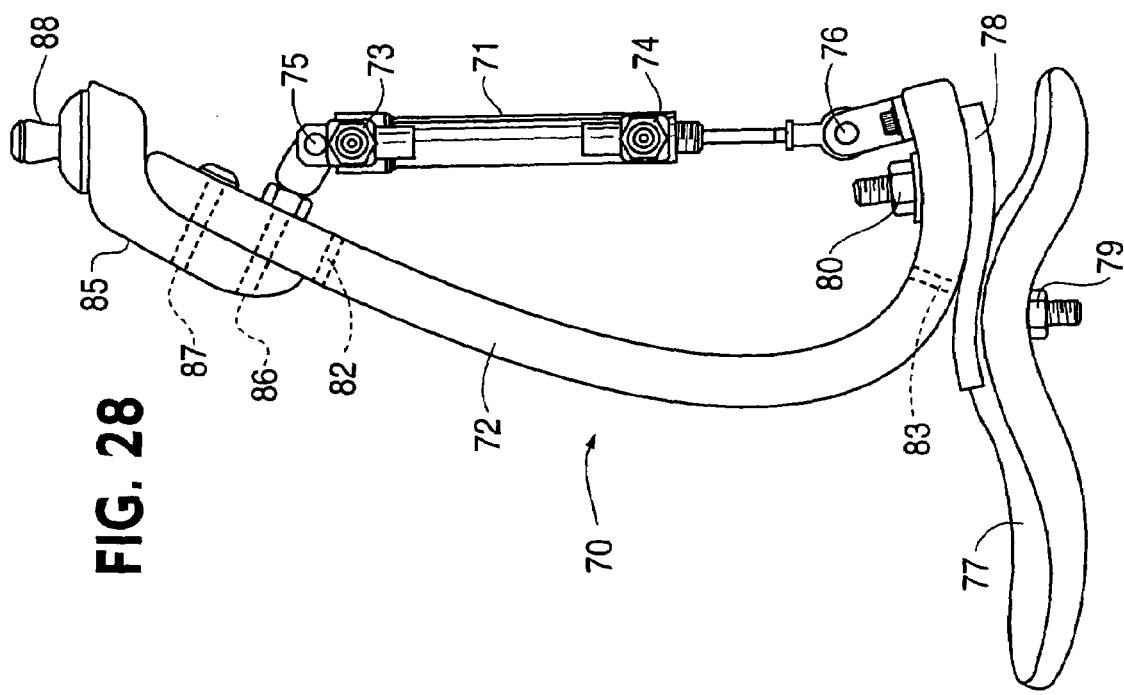
FIG. 28 is a side view of a further example embodiment of the prosthetic foot similar to those in FIGS. 3 and 25 wherein a motion limiting, dampening device is connected between respective ends of the calf shank to limit the extent of the motion of the upper end of the calf shank in response to force loading and unloading the calf shank during use of the prosthetic foot.
Figure 30:
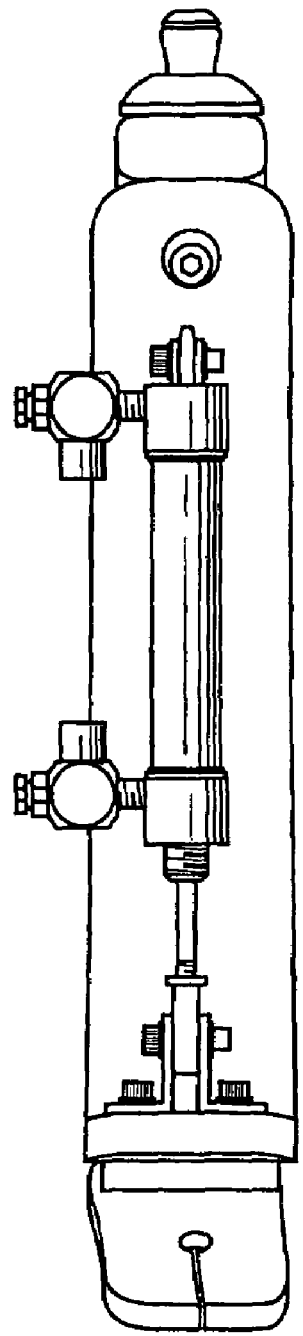
FIG. 30 is a rear view of the prosthetic foot, as seen from the right side of the prosthetic foot shown in FIG. 28.

The longitudinally extending foot keel 77 of the prosthetic foot 70 in FIGS. 28-32 has forefoot, midfoot and hindfoot portions like the foot keels in FIGS. 3 and 25. The calf shank 72 of the foot is attached to the foot keel by a coupling element 78 with two releasable fasteners 79 and 80 spaced longitudinally connecting the coupling element to the calf shank and foot keel, respectively, as in the example embodiment of FIGS. 25-27. The calf shank 72 includes a longitudinally extending expansion slot 81 intermediate the ends of the calf shank. Expansion joint holes 82 and 83 are located at the ends of the expansion slot. The forefoot and hindfoot portions of the foot keel are also formed with respective expansion slots as seen in FIGS. 29, 30 and 31.

A prosthetic socket attached to the amputee's lower leg stump is connected to the upper end of calf shank 72 via an adapter 85 secured to the upper end of the calf shank by fasteners 86 and 87 as shown in the drawings. The adapter has an inverted pyramid-shaped attachment fitting 88 connected to an attachment plate attached to an upper surface of the adapter. The pyramid fitting is received by a complementarily shaped socket-type fitting on the depending prosthetic socket for joining the prosthetic foot and prosthetic socket. This type of connection is shown in the embodiment of FIGS. 34-36.

While the motion limiting, dampening device 71 in the example embodiment of FIGS. 28-32 limits the extent of the motion of the upper end of the calf shank in both compression and expansion of the calf shank, a similar device which only limits the extent of motion of the upper end of the calf shank in one of compression and expansion could be employed. A motion limiting, dampening device 84 restricting only the expansion of the upper end of the calf shank with forced loading and unloading is shown in the example embodiment of FIG. 33. The device 84 therein is a flexible strap which allows limited, elastic extension of the strap and thereby expansion of the calf shank while not limiting the motion of the upper end of the calf shank in compression loading of the calf shank. This elastic device 84 can be tensioned in its application whereby the elastic device predisposes the proximal end of the shank to move posteriorly.

FIGS. 34-36 illustrate another calf shank 90 of the invention which can be used with the foot keel 77 of the prosthetic foot in FIGS. 28-32 or with one of the other foot keels disclosed herein. The calf shank 90 has a generally parabola shape with the smallest radius of curvature thereof located at the lower end and extending upwardly, and initially anteriorally into relatively larger radii at the proximal terminal end thereof. A posterior facing concavity is formed by the curvature of the calf shank as depicted in FIG. 34. The distal end of the calf shank has a longitudinally extending opening 91 which, together with coupling element 78, releasable fasteners 79 and 80 and a longitudinally extending opening in the foot keel permit adjusting the alignment of the calf shank and the foot keel with respect to one another in the longitudinal direction when the fastener 79 or 80 is loosened or released for tuning the performance of the prosthetic foot to be task specific.

The distal end of the calf shank 90 is more sharply curved, e.g., has a smaller radius of curvature, than the calf shank 72 in FIGS. 28-32, and extends upwardly and anteriorly in a shorter longitudinal distance. This calf shank shape is more cosmetically friendly. That is, its distal end is located more in the ankle region, where the medial and lateral malleoli of a human foot shaped outer covering of the prosthetic foot would normally be located. The calf shank tucks in the outer prosthetic foot covering better. Its functional characteristics are that it responds quicker to initial contact ground reaction forces, although with less dynamic response capability than a calf shank with a wider parabola, e.g., longer radii of curvature as noted above. Thus, those active persons who run and jump with a prosthetic foot would benefit from using a wider parabola or radius of curvature which affords a greater horizontal velocity.

The calf shank 90 of FIGS. 34-36 further includes an alignment coupler device 92 located intermediate a plastic or metal adapter 93 connected to the upper end of the calf shank by fasteners 94 and 95, and the lower end of a prosthetic socket 96 secured to the leg stump of the user. The user could be an above the knee or a below the knee amputee, for example. The alignment coupler device contains a pair of slides 97 and 98 arranged at right angles to each other and in planes parallel to the ground. The relative position of the components of each slide can be adjusted by loosening threaded fasteners 99 for adjusting the respective slides 97 and 98 to change of the relative orientation of the prosthetic socket to the calf shank and foot keel of the prosthetic foot. The top of the adapter 93 supporting the device 92 is preferably parallel to the ground in the stance phase of gait with the prosthetic foot.

The top of the upper slide 98 of the device 92 has an inverted pyramid shaped fitting 101 secured thereon which is adjustably clamped in a corresponding fitting 102 on the prosthetic socket 96 by means of threaded fasteners 103. This connection between fitting 101 and 102 allows for angular change-flexion/extension and abduction/adduction between the prosthetic socket and foot. The slides of device 92 allow medial-lateral and anterior-posterior linear, sliding adjustments. Thus, the device 92 is an alignment fixture which allows the prosthetic socket to be moved in all directions, which influences how the ground reaction forces respond to the calf shank and foot keel mechanical structures.

Figure 37:
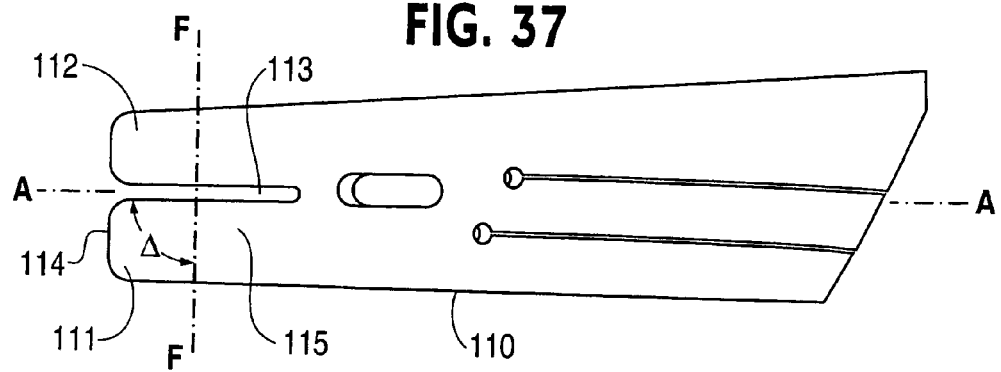
FIG. 37 is a top view of another foot keel for a prosthetic right foot of the invention wherein the posterior end of the foot is parallel to the frontal plane, e.g., perpendicular to the longitudinal axis A-A of the foot, and the longitudinal axis F-F of a proximal hindfoot concavity is also perpendicular to the longitudinal axis A-A.
Figure 38:
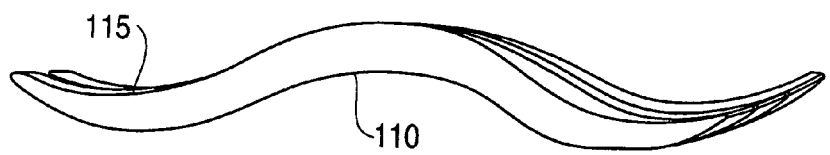
FIG. 38 is a side of the foot keel of FIG. 37 as seen in the direction from the lateral side of the foot keel.
Figure 39:
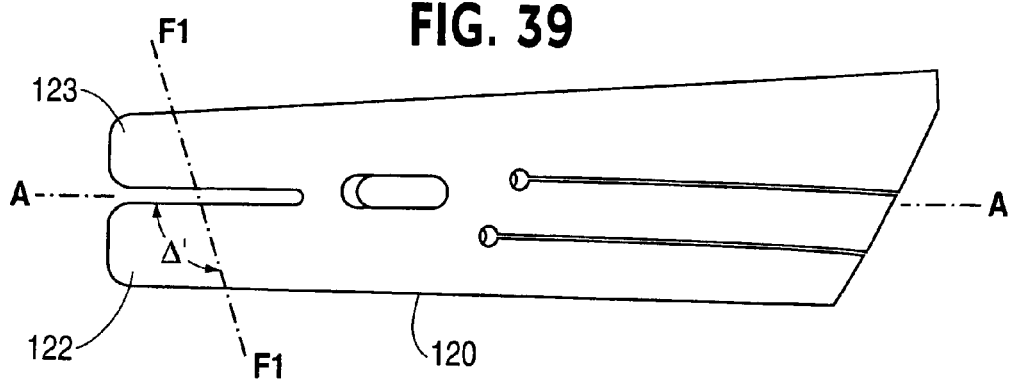
FIG. 39 is a top view of an additional foot keel of the invention similar to that in FIGS. 37 and 38, but having a longitudinal axis F'-F' of its proximal hindfoot concavity at an obtuse angle Δ' to the longitudinal axis A-A which renders the lateral strut of the hindfoot effectively longer and more flexible than the medial strut to aid eversion of the foot on heel contact in gait.
Figure 40:
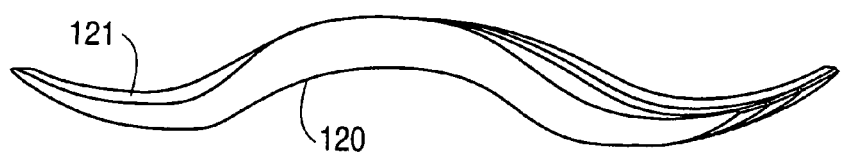
FIG. 40 is a side view of the foot keel of FIG. 39 as seen from the lateral side of the foot keel.

The foot keel 110 in FIGS. 37 and 38 and the foot keel 120 of FIGS. 39 and 40 are further example embodiments foot keels which can be used in the prosthetic foot of the invention. The foot keels are for the right foot and have similar constructions except in the hindfoot portion. The medial and lateral sides of the two foot keels are the same shape. Foot keel 110 is sagittally cut in the hindfoot area with identical lateral and medial expansion struts 111 and 112 separated by a longitudinally extending expansion joint or slot 113. The posterior terminal heel area 114 of the foot keel 110 is parallel to the frontal plane, e.g., perpendicular to the longitudinal axis A-A of the foot keel. Similarly, the hindfoot dorsal concavity 115 of the foot keel has its longitudinal axis F-F parallel to the frontal plane, e.g., at right angles to the longitudinal axis A-A, i.e., angle $\Delta$ is 90°.

Foot keel 120, in contrast to foot keel 110, is not sagittally cut in the hindfoot area but has its hindfoot dorsal concavity 121 cut such that the longitudinal axis F'-F' of the concavity is skewed transverse to the frontal plane, e.g., makes an obtuse angle $\Delta'$ with the longitudinal axis A-A of preferably 110-125° with the lateral side further anterior than the medial side. This orientation of the dorsal concavity makes the lateral expansion strut 122 thinner over a greater length than the medial expansion strut 123, and thereby effectively longer and more flexible than strut 123. This increase in flexibility predisposes the hindfoot to respond to initial contact ground reaction forces by everting—which is a shock absorption mechanism. This aids in efficiently transferring the forces of the body's center of gravity through the hindfoot of the foot keel in gait for achieving a more normal gait pattern.

Figure 41:
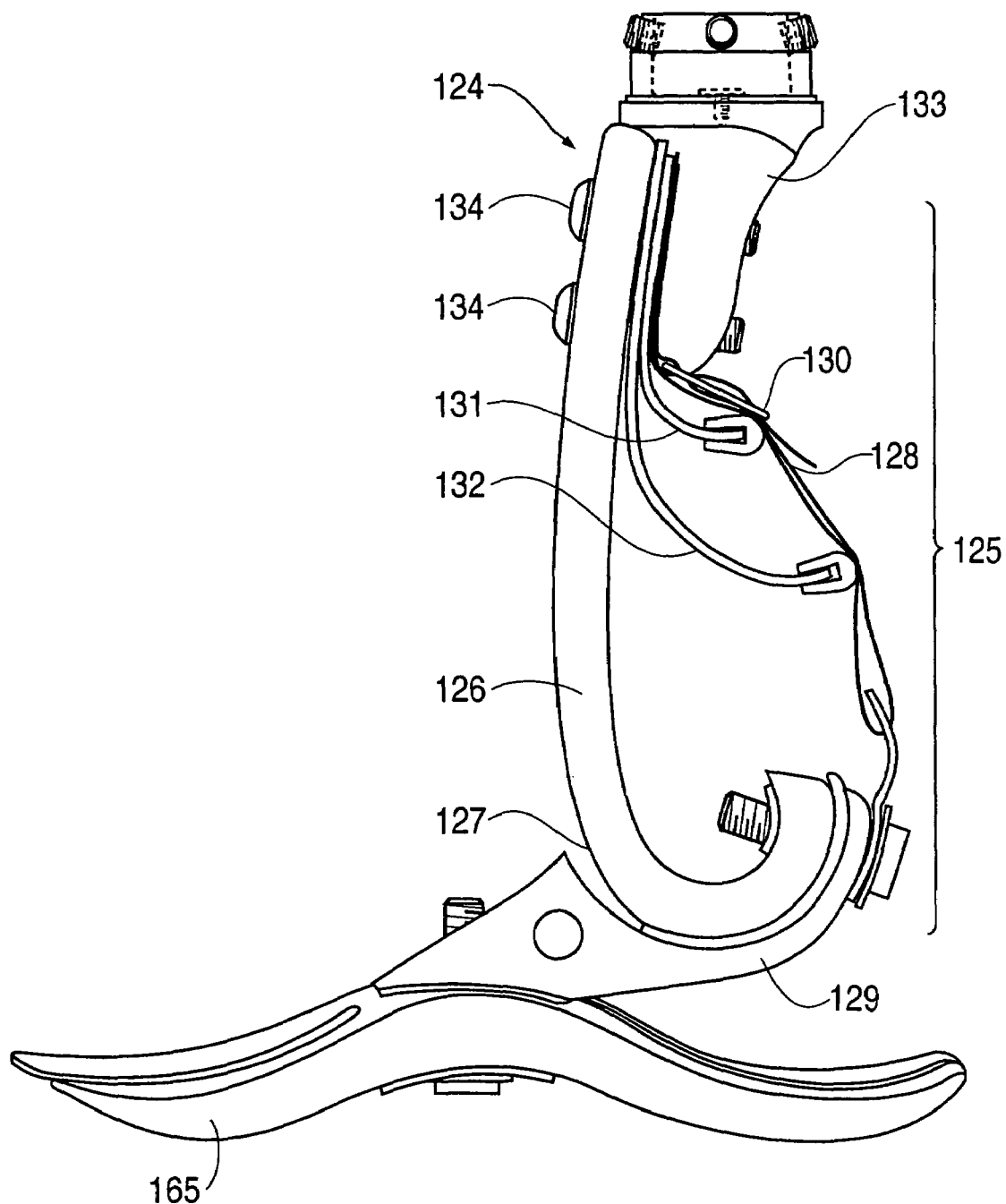
FIG. 41 is a side view of an additional embodiment of the prosthetic foot having a resilient posterior calf device connected between an upper portion of the calf shank and the coupling element connecting the calf shank to the foot keel, the device storing energy in springs of the device during force loading in gait and returning the stored energy during force unloading to increase the kinetic power generated for propulsive force by the prosthetic foot in gait.
Figure 42:
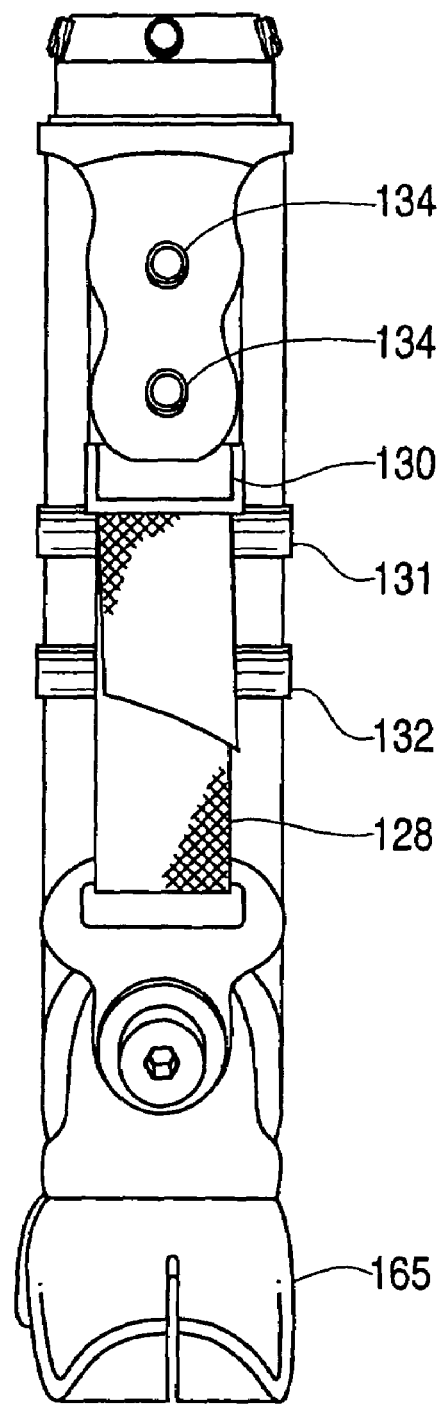
FIG. 42 is a rear view of the prosthesis of FIG. 41.

A prosthetic foot 124 in FIGS. 41 and 42 has a foot keel 165, a calf shank 126 and a posterior calf device 125 to store additional energy with anterior motion of the upper end of the calf shank in gait. That is, in the active propulsion phase of gait force loading of the resilient prosthesis expands the sagittal plane concavity of the shank 126 formed by the anterior facing convexly curved portion 127 of the calf shank which results in anterior movement of the upper end of the calf shank. A flexible strap 128 of the device 125 is connected to an upper portion of the calf shank and a lower portion of the prosthetic foot, namely to coupling element 129 which connects the calf shank and foot keel as disclosed above. The length of the flexible strap, which can be elastic and/or non-elastic is tensioned in gait and can be adjusted by use of a slide adjustment 130 between overlapping lengths of the strap.

Two springs 131 and 132 are adjustably supported at their bases on the upper end of the calf shank between the calf shank and adapter 133 secured to the calf shank with fasteners 134. The lower, free ends of the springs are positioned to interact with the flexible strap. When the strap is tensioned the springs change the direction of the longitudinal extent of the strap. Anterior movement of the upper end of the calf shank in gait tensions/further tensions (if the strap is initially preloaded in tension) the strap and loads/further loads the springs to store energy in force loading of the prosthetic foot in gait. This stored energy is returned by the springs in force unloading of the prosthetic foot to increase the kinetic power generated for propulsive force by the prosthetic foot in gait.

When the strap 128 is shortened to initially preload the strap in tension prior to use of the prosthetic foot, the strap tension serves to assist posterior movement of the upper end of the resilient member as well as control anterior movement of the calf shank during use of the prosthesis. Assisting the posterior movement can be helpful in attaining a rapid foot flat response of the prosthetic foot at heel strike in the initial stance phase of gait akin to that which occurs in a human foot and ankle in gait at heel strike where plantarflexion of the foot occurs.

The assisting posterior movement of the upper end of the resilient calf shank and the controlling anterior movement of the upper end of the resilient calf shank during use of the prosthesis using the posterior calf device 125 are each effective to change the ankle torque ratio of the prosthetic foot in gait by affecting a change in the sagittal plane flexure characteristic for longitudinal movement of the upper end of the calf shank in response to force loading and unloading during a person's use of the prosthetic foot. The natural physiologic ankle torque ratio in the human foot in gait, defined as the quotient of the peak dorsiflexion ankle torque that occurs in the late terminal stance of gait divided by the plantar flexion ankle torque created in the initial foot flat loading response after heel strike in gait has been reported as 11.33 to 1. An aim of changing the sagittal plane flexure characteristic for longitudinal movement of the upper end of the calf shank using the posterior calf device 125 is to increase the ankle torque ratio of the prosthesis to mimic that which occurs in the human foot in gait. This is important for achieving proper gait with the prosthesis and, for a person with one natural foot and one prosthetic foot, for achieving symmetry in gait. Preferably, through controlling anterior movement and possibly assisting posterior movement using the posterior calf device 125, the ankle torque ratio of the prosthesis is increased so that the said peak dorsiflexion ankle torque which occurs in the prosthesis is an order of magnitude greater than said plantar flexion ankle torque therein. More preferably, the ankle torque ratio is increased to a value of about 11 to 1, to compare with the reported natural ankle torque ratio of 11.33 to 1.

A further purpose of the posterior calf device is to improve the efficiency of the prosthetic foot in gait by storing additional elastic energy during force loading of the prosthesis in the springs 131 and 132 of the device and to return the stored elastic energy during force unloading to increase the kinetic power generated for propulsive force by the prosthetic foot in gait. The device 125 may be considered to serve the purpose in the prosthetic foot that the human calf musculature serves in the human foot, ankle and calf in gait, namely efficiently generating propulsive force on the person's body in gait utilizing the development of potential energy in the body during force loading of the foot and the conversion of that potential energy into kinetic energy for propulsive force during force unloading of the foot. Approaching or even exceeding the efficiencies of the human foot in the prosthetic foot of the invention with the posterior calf device is important for restoring "normal function" to an amputee, for example.

The control of anterior movement of the upper end of the calf shank 126 by the posterior calf device 125 is effective to limit the range of anterior movement of the upper end of the calf shank as in the previous embodiments of FIGS. 28-33. The foot keel in the prosthetic foot 124 by the expansion of its resilient longitudinal arch also contributes to storing energy during force loading in gait. This potential energy is returned as kinetic power for generating propulsive during force unloading in gait. In the embodiment there is a high low dynamic response capability as a result of the foot keel's midfoot portion being formed with a longitudinal arch with a medial aspect larger in radius and with a relatively higher dynamic response capability than a lateral aspect of the arch as discussed above in connection with the embodiments of FIGS. 3-5 and 8. However, a foot keel for sprinting as in FIGS. 6 and 7 or a foot keel for a Symes amputation of the foot as referred to in the discussion of FIGS. 9 and 10 could be used in the prosthetic foot 124.

Figure 43:
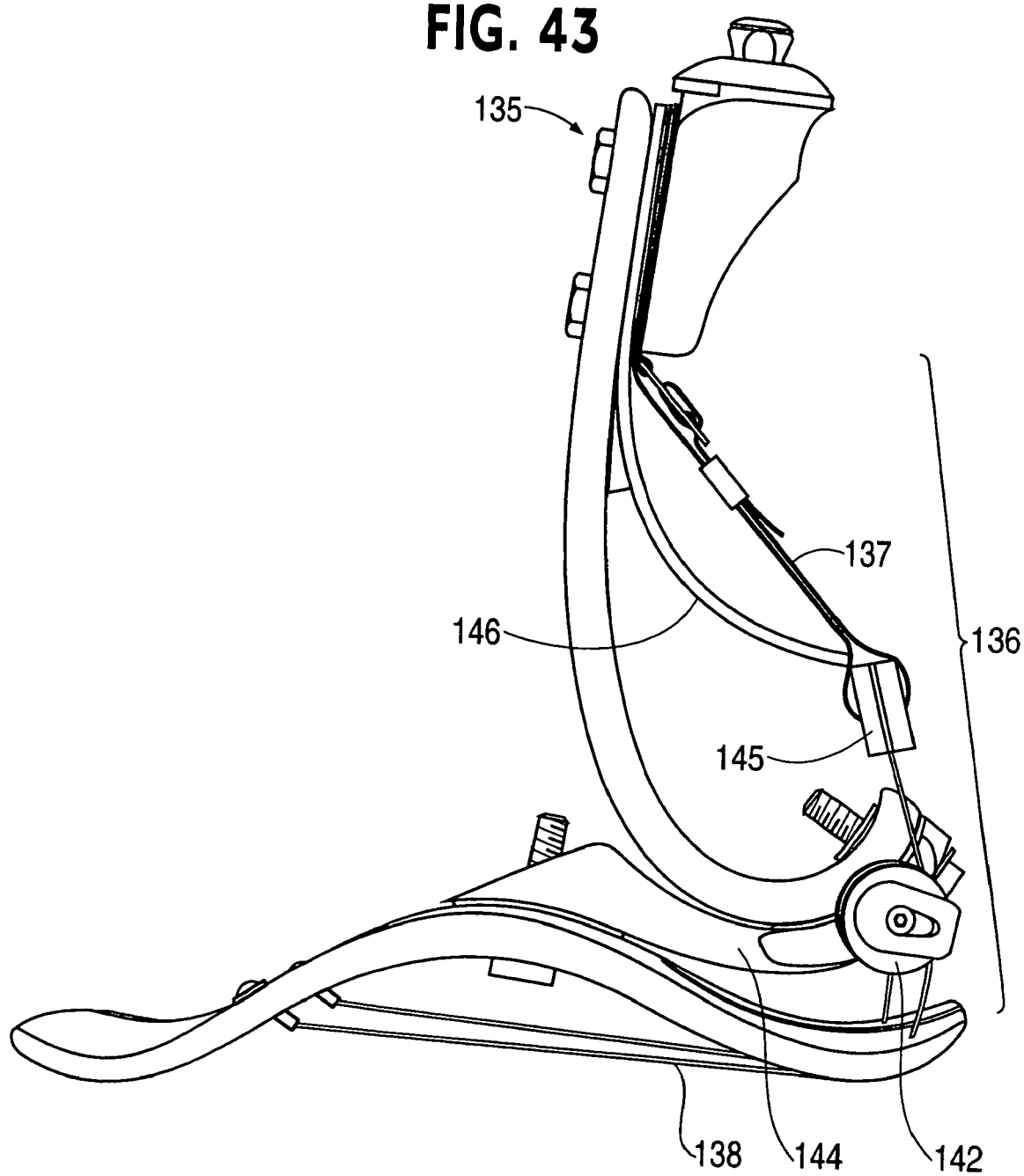
FIG. 43 is a side view of a further embodiment of the prosthetic foot having a posterior calf device for increasing the kinetic power generated for propulsive force by the prosthetic foot in gait wherein a adjustable length strap of the device is tensioned between an upper portion of the calf shank and the anterior end of the foot keel.
Figure 44:
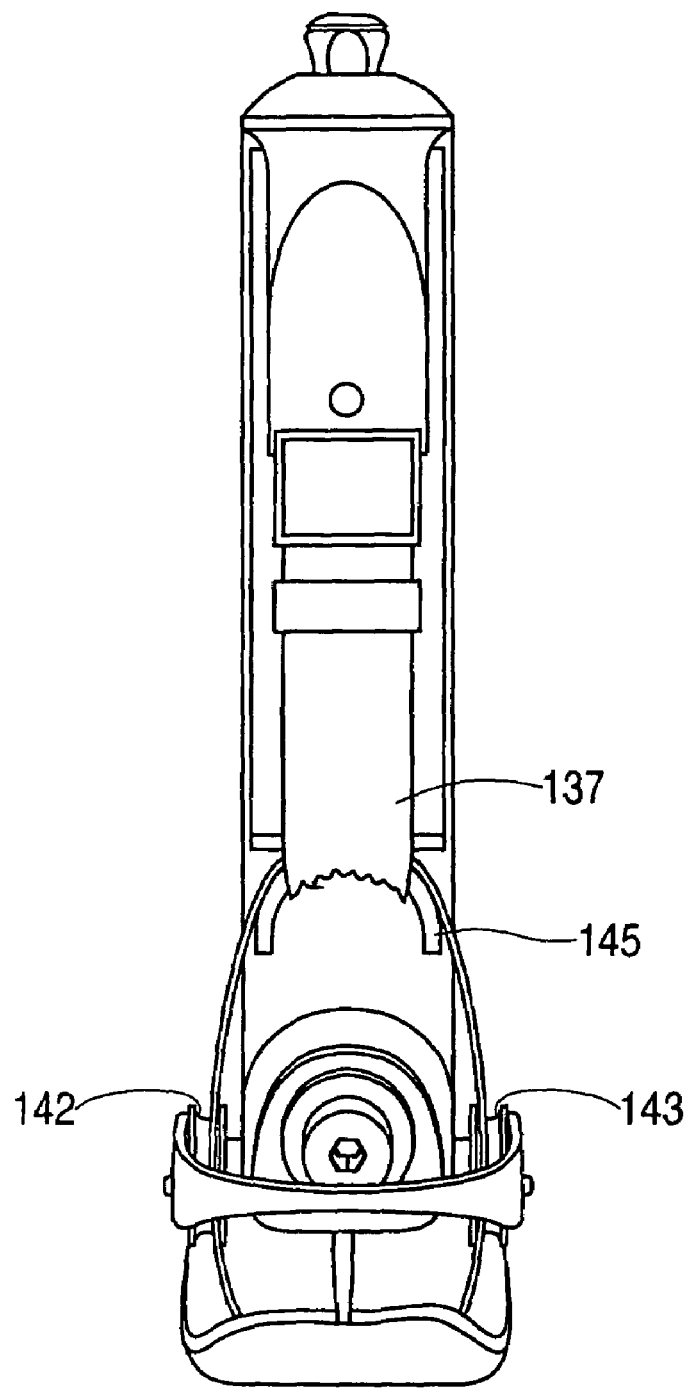
FIG. 44 is a rear view of the prosthesis of FIG. 43.
Figure 45:
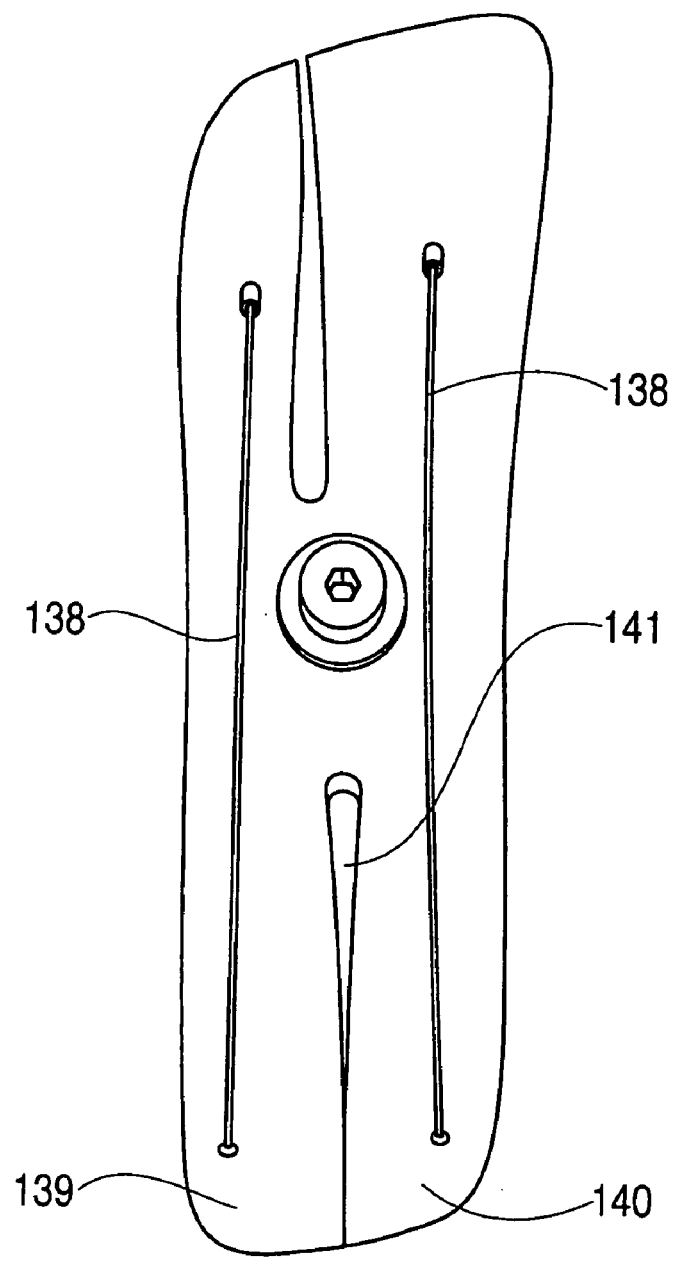
FIG. 45 is a bottom view of the prosthesis of FIGS. 43 and 44 showing the tensioning cable connected to each side of the foot keel and extending posteriorly.

The prosthetic foot 135 depicted in FIGS. 43-45 has a posterior calf device 136 similar to that in the embodiment of FIGS. 41 and 42 except that the adjustable length flexible strap 137 is connected between the upper end of the calf shank and the anterior of the foot keel by way of a connecting cable 138. The ends of the cable 138 are connected to respective ones of medial and lateral anterior struts 139 and 140, separated by expansion joint 141. The cable extends posteriorly and then upwardly by way of pulleys 142 and 143 mounted on coupling element 144 to a semicircular return 145 connected to the distal end of the strap 137. The resilient arch of the foot keel as well as a spring 146, mounted on the upper end of the calf shank and engaging the strap as in the embodiment of FIGS. 41 and 42, are used to store and return energy for adding to the propulsive force generated by the prosthetic foot in gait as discussed above.

The adapter 133 in FIG. 43 is a male pyramid adapter while that in FIGS. 41 and 42 is a female adapter of the present invention having a square socket, with rounded corners, in its proximal end for receiving with clearance a square complementarily shaped projection on the lower extremity socket or other component on the amputee's leg stump. See the dashed lines in FIG. 41. Four screws, not numbered, one in the middle of each side wall of the square socket can be screwed into and out of engagement with the projection for connecting the prosthesis to the supporting structure on the amputee's leg stump. The clearance between the projection and the socket and the adjustability of the positions of the four screws of the female adapter permit anterior-posterior and medial-lateral adjustability and also angular or tilt adjustment of the prosthesis and supporting structure. According to a further feature of the female adapter, a threaded fastener releasably connects the upper, socket containing member of the adapter with the underlying base of the adapter. The top of the threaded fastener, exposed in the base of the socket of the adapter, has an Allen socket for receiving an Allen wrench to permit loosening the adapter socket containing member on the base so that it can be rotated relative to the base and the prosthesis. Thus, the adapter provides transverse plane rotation capability; a feature that allows for easy toeing in and out of the foot to within critical limits, e.g. to within ⅛ inch.

Figure 46:
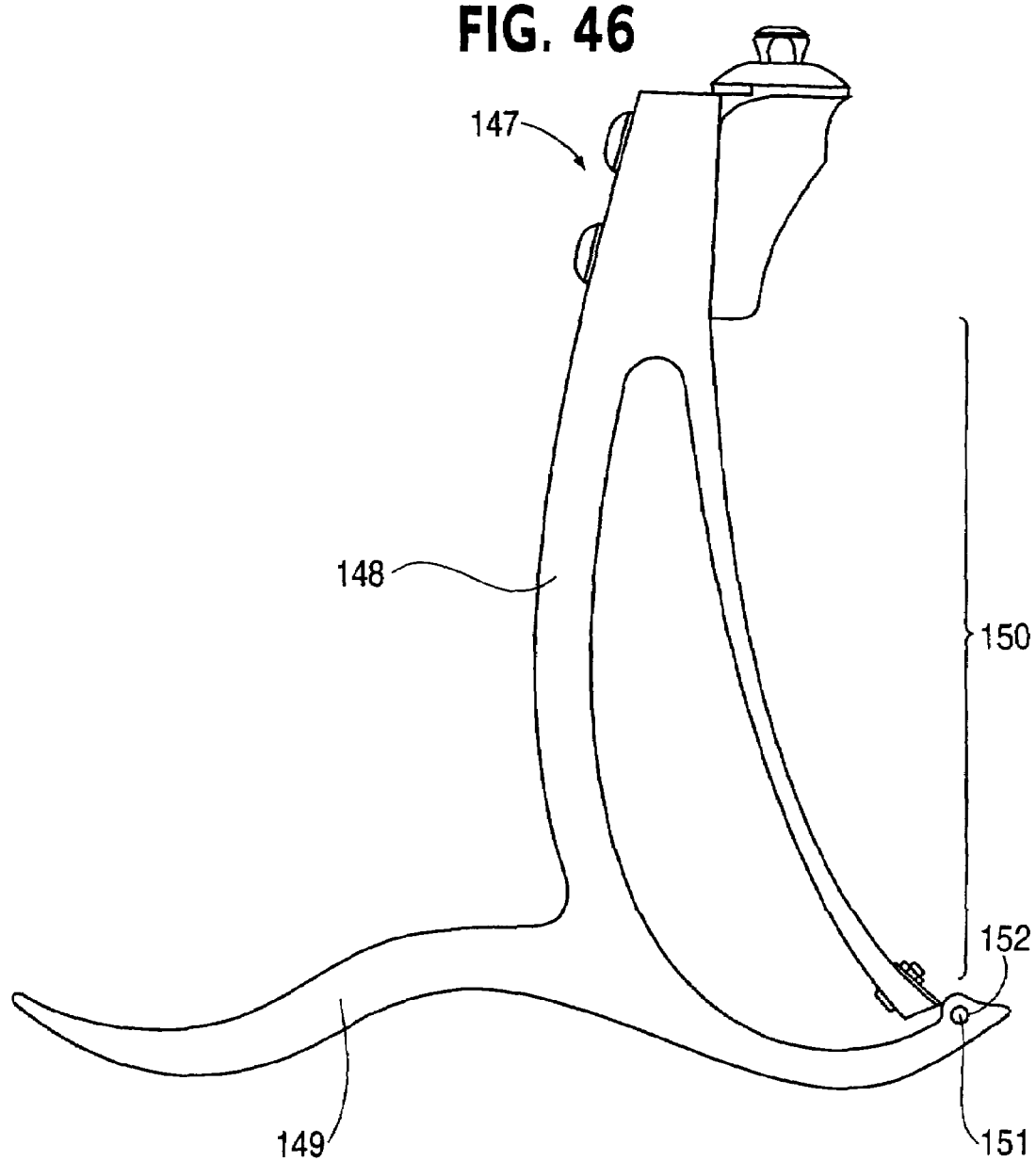
FIG. 46 is a side view of another embodiment of the prosthetic foot wherein the calf shank and foot keel and also the posterior calf device are monolithically formed, the distal end of the spring of the device being pivotably connected to the posterior of the foot keel.
Figure 47:
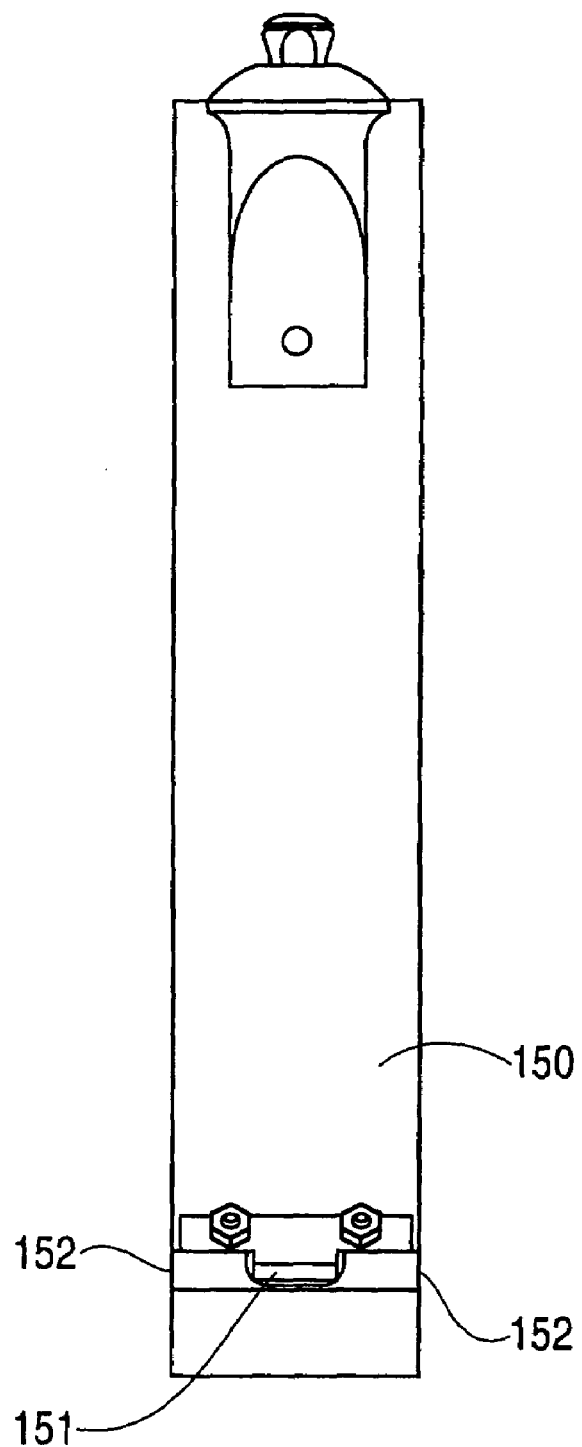
FIG. 47 is a rear view of the prosthesis of FIG. 46.
Figure 48:
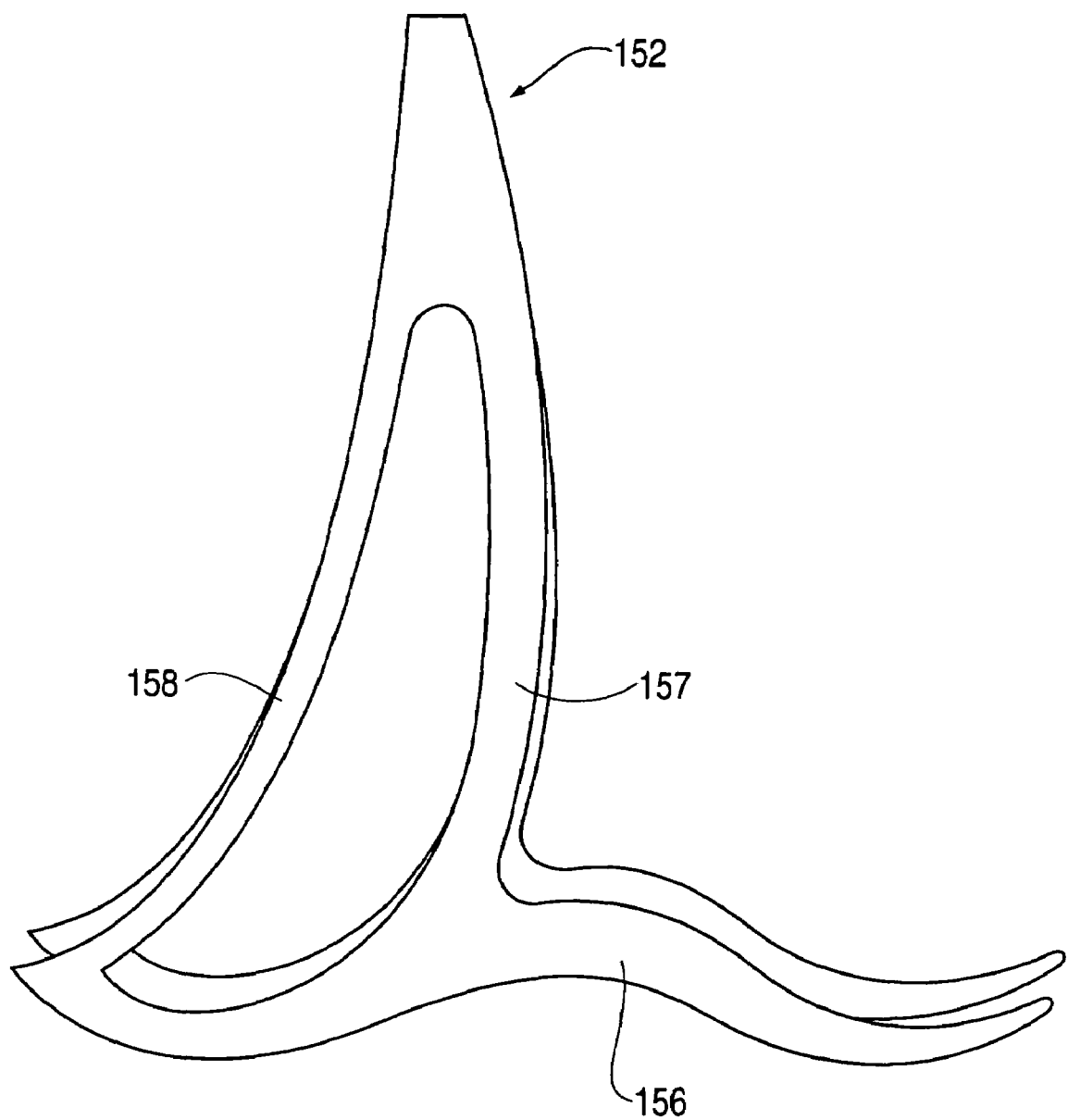
FIG. 48 is a side view of an embodiment of the prosthetic foot similar to that in FIGS. 46 and 47 but where the foot keel, calf shank and posterior calf device are monolithically formed with three, side by side longitudinal sections freely movable with respect to one another at their distal ends but connected at the proximal end of the calf shank, with the center section being wider, and at its distal surface higher, than the outer sections.
Figure 49:
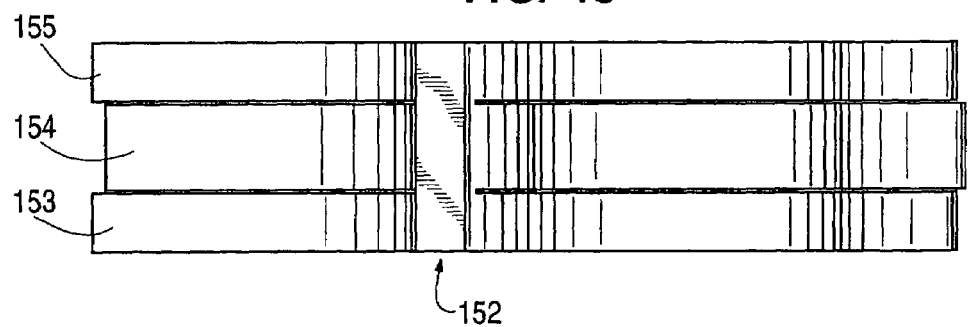
FIG. 49 is a top view of the prosthesis of FIG. 48.
Figure 50:
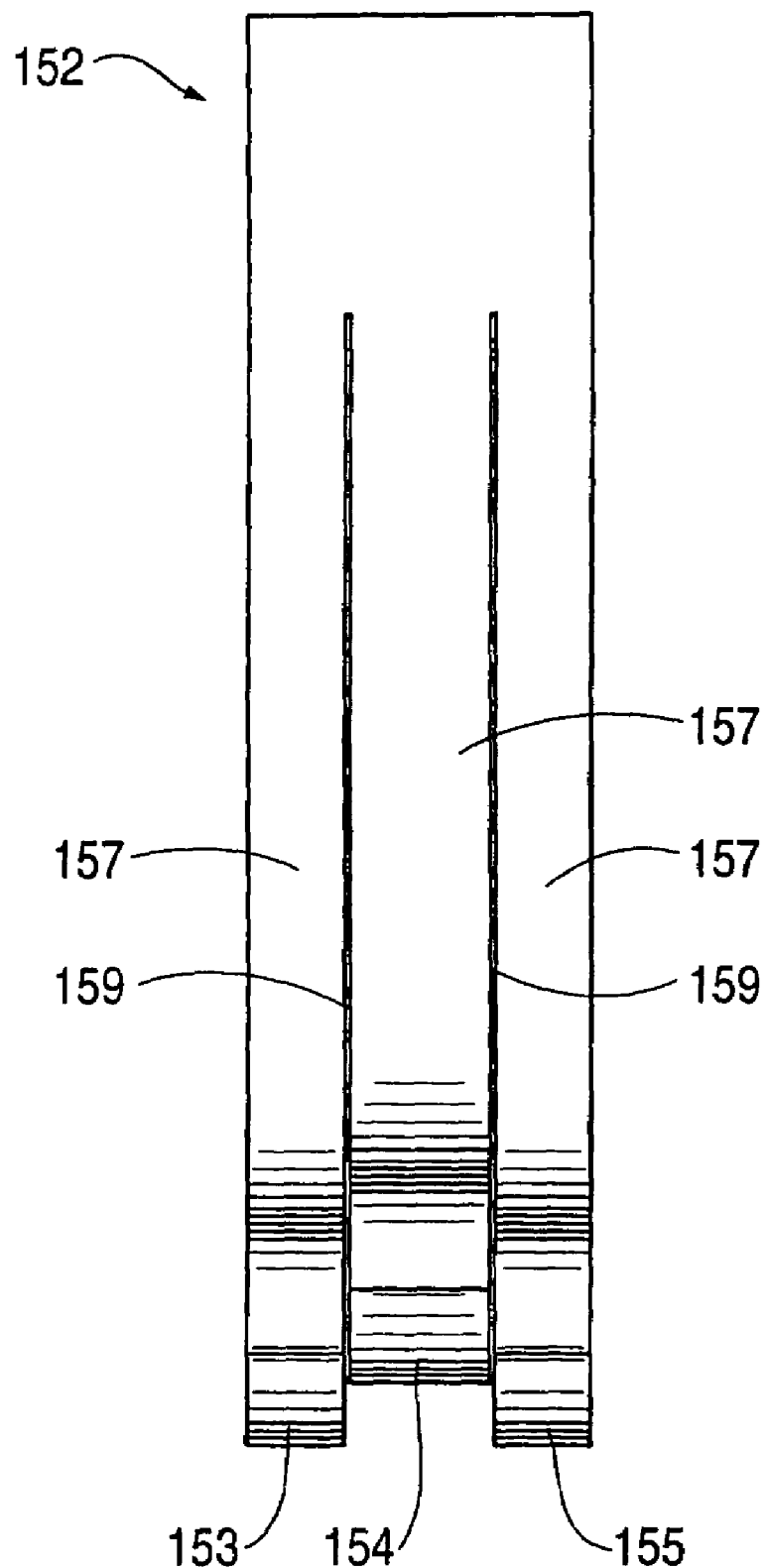
FIG. 50 is a front view of the prosthesis of FIGS. 48 and 49.
Figure 51:
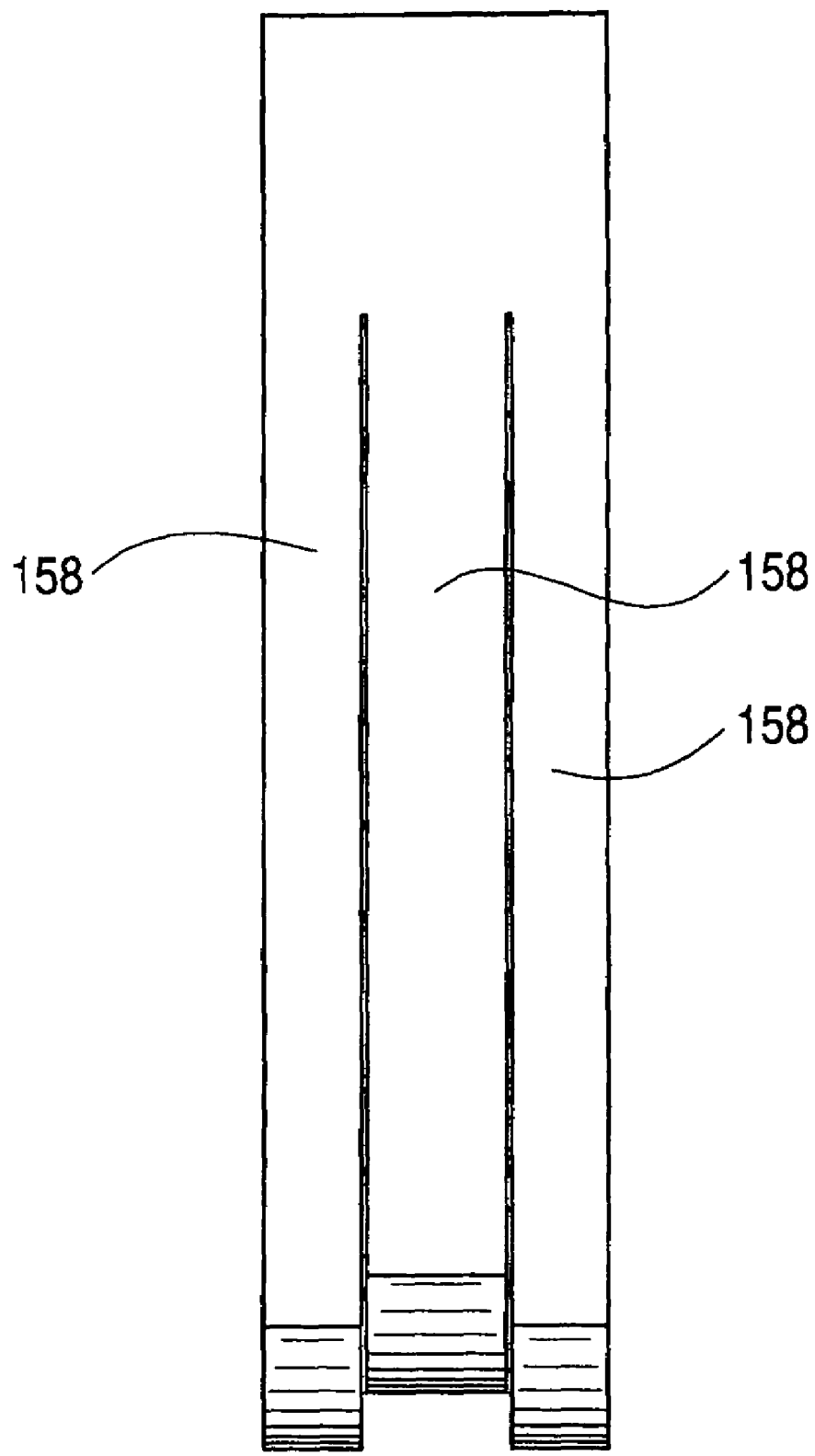
FIG. 51 is a rear view of the prosthesis of FIGS. 48-50.

The prosthetic foot 147 in the embodiment of FIGS. 46 and 47 is characterized by a calf shank 148, foot keel 149 and posterior calf device 150 which are monolithically formed. The calf shank 148 has an anterior facing convexly curved lower portion extending upwardly from the foot keel as in previously described embodiments. The posterior calf device 150 is in the form of an elongated, resilient, curved spring connected at its proximal end to an upper portion of the calf shank and at its distal end the spring is pivotably connected to a posterior portion of the foot keel by a bracket with pivot pin 151 mounted on the distal end of the spring with the pin extending through an aperture 152 in the posterior end of the foot keel. The ends of pin 151 are anchored in the openings 152 in the foot keel as shown in the drawings. With anterior or posterior motion of the upper end of the calf shank in gait, the concavity of the curved spring will be expanded or compressed to store energy within the motion limits of the spring. The stored energy will then be returned upon force unloading in gait to add to the kinetic power available for propulsive force of the user's body.

The embodiment in FIGS. 48-51 is a prosthetic foot 152 having three longitudinal sections 153-155. Each longitudinal section is monolithically formed with a foot keel 156, calf shank 157 and posterior calf device 158. The sections 153-155 are movable independent of one another at their distal ends, where they are separated by gaps 159, but the sections are integral at their proximal ends, e.g. at the upper end of the calf shank. This integral construction can be provided by use of fasteners for connecting the proximal ends of the respective, separately formed longitudinal sections to one another. Alternatively, the resilient longitudinal sections can be monolithically formed with one another such that they are connected at their upper ends while freely movable relative to each other at their distal ends where gaps 159 separate the sections.

The center longitudinal section 154 in the prosthesis 152 is wider than the medial and lateral sections 153 and 155 and also, at its distal end, it is higher than the sections 153 and 155. This construction provides advantages in support on uneven or inclined surfaces as discussed previously in connection with the use of a plurality of longitudinal anterior and posterior foot keel struts separated by expansion joints. The number of the plurality of longitudinal sections employed in the prosthesis can be other than three and the relative widths of the sections can be varied from that shown in the embodiment. The distal end of the curved spring of posterior calf device 158 of each longitudinal section is formed integrally with the hindfoot of its foot keel 156 rather than being pivotably connected thereto as in the embodiment of FIGS. 46 and 47. A suitable adapter, not shown, is connected to the upper end of the calf shank of the prosthesis 152 for connection with a lower extremity socket on the leg stump of the user as described and illustrated in the other embodiments.

Figure 52:
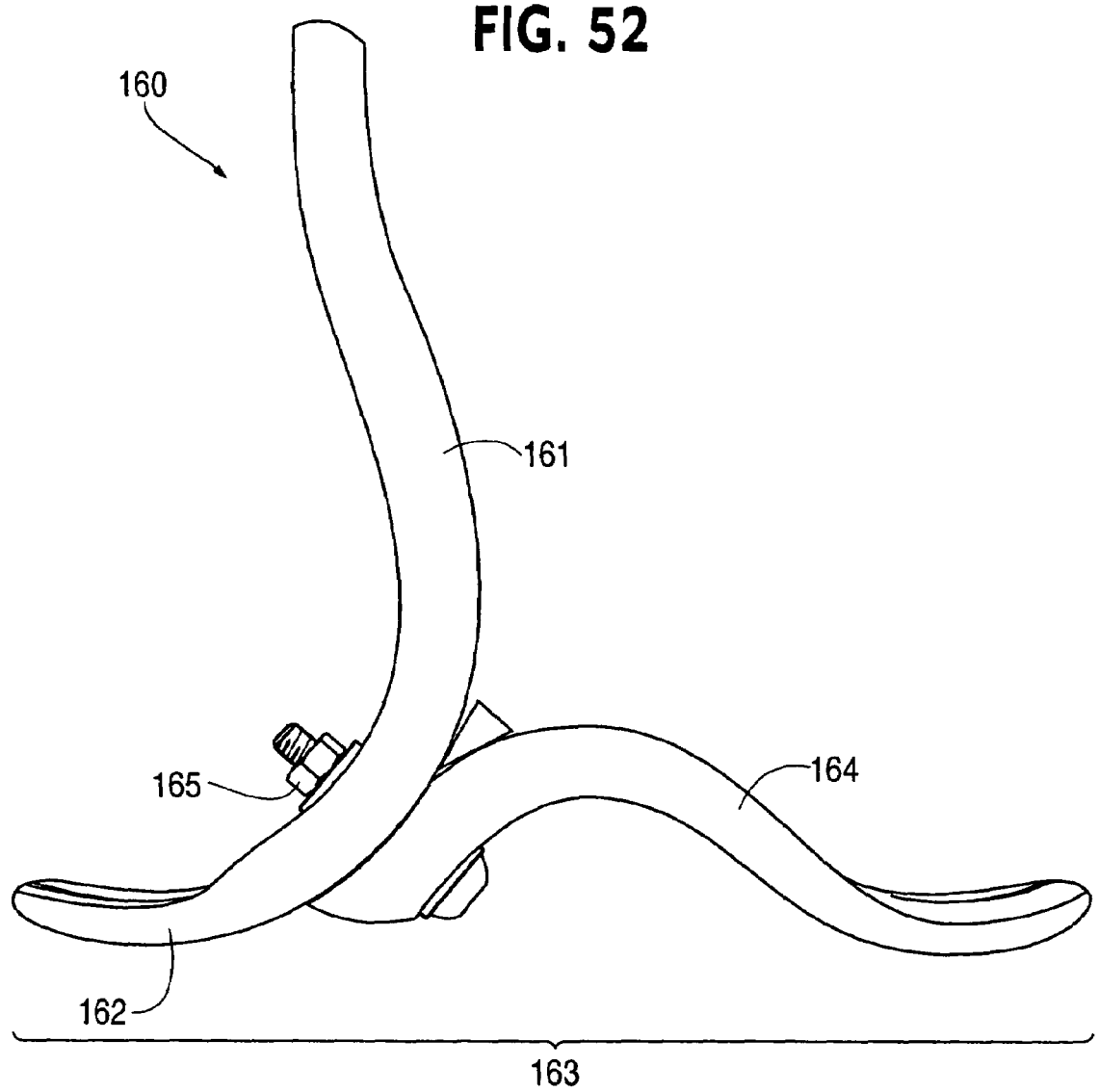
FIG. 52 is a side view of another form of the calf shank and foot keel of the invention wherein the shank is monolithically formed with a posterior portion of the foot keel, which is connected by fasteners to a forefoot and midfoot forming member of the prosthesis.
Figure 53:
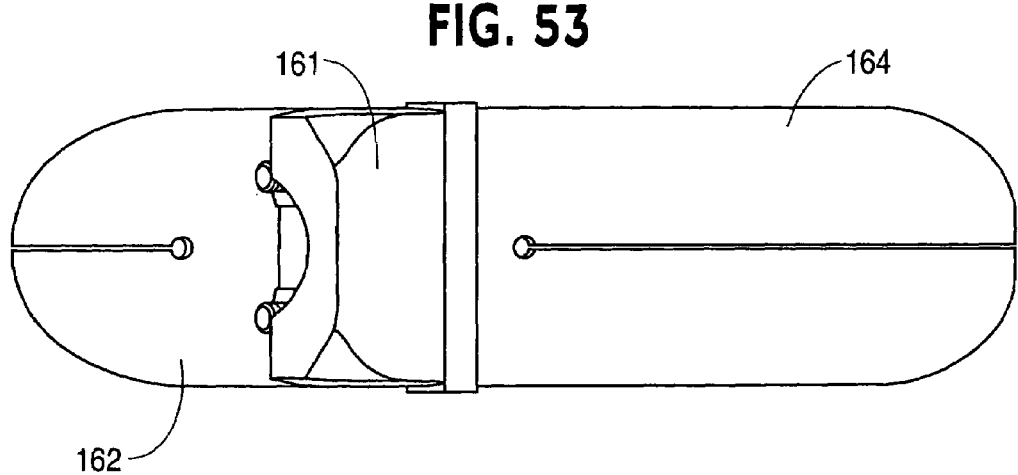
FIG. 53 is a top view of the calf shank and foot keel of FIG. 52.
Figure 54:
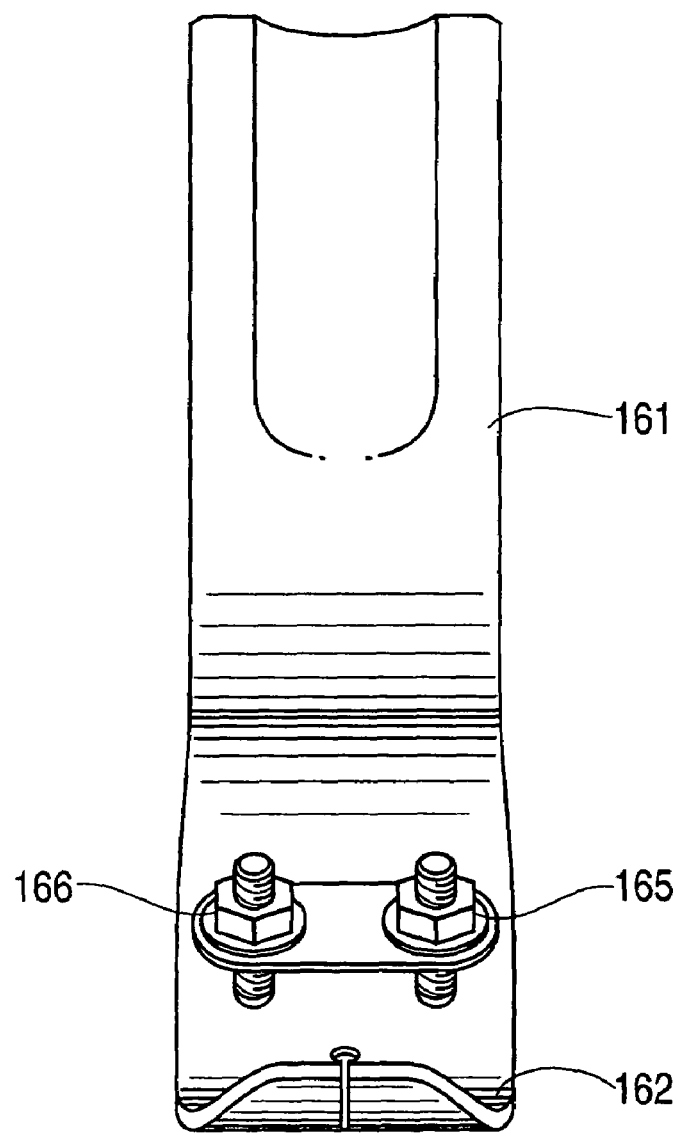
FIG. 54 is a rear view of the calf shank and foot keel of FIGS. 52 and 53.

Another form of construction for the prosthetic foot of the invention is illustrated in FIGS. 52-54 wherein the prosthetic foot 160 comprises a calf shank 161 monolithically formed with a posterior portion 162 of foot keel 163. The resilient member of the shank and hindfoot is connected to a resilient member 164 forming forefoot and midfoot portions of the foot keel by fasteners 165 and 166 as shown in the drawings. A posterior calf device, not shown in FIGS. 52-54, can be formed as part of the prosthesis as disclosed above. Likewise, an adapter for connection to a lower extremity socket is to be attached to the upper end of the calf shank 161.

This concludes the description of the example embodiments. Although the present invention has been described with reference to a number of illustrative embodiments, it should be understood that numerous other modifications and embodiments can be devised by those skilled in the art that will fall within the spirit and scope of the principles of this invention. For example, the lower end of the calf shank in the prosthetic foot of the invention is not limited to a parabola shape or a generally parabola shape but can be otherwise downward convexly, curvilinearly configured to produce the desired motion outcomes of the foot when connected to the foot keel to form the ankle joint area of the foot. The features of the various embodiments could also be used with one another. More particularly, reasonable variations and modifications are possible in the component parts and/or arrangements of the subject combination arrangement within the scope of the foregoing disclosure, the drawings, and the appended claims without departing from the spirit of the invention. In addition to variations and modifications in the component parts and/or arrangements, alternative uses will also be apparent to those skilled in the art.

We claim:

1. A prosthetic foot comprising:
  a continuously longitudinally extending foot keel having longitudinally aligned forefoot, raised midfoot, and hindfoot portions;
  a resilient, monolithically formed shank extending upwardly from the raised midfoot portion of the foot keel, by way of an anterior facing continuous convexly curved surface which extends over at least most of the length of the shank and has increasing radius of curvature defining an ankle joint area and a curvilinear prosthetic part of a leg extending substantially upward above human ankle joint height and the ankle joint area, the shank having a proximal portion for connection with a lower extremity prosthetic structure adapted to be secured to a person's residual limb;
  wherein the ankle joint area and the prosthetic part of a leg formed by the shank are anterior facing convexly curved and provide means for sagital, anterior dorsiflexion and, posterior plantarflexion motion capabilities in response to a ground reaction force created in a person's gait in the prosthetic foot;
  wherein the shank and the entire foot keel are monolithically formed; and wherein the anterior facing continuous convexly curved surface extends the entire length of the ankle joint area and curvilinear prosthetic part of a leg defined by the shank.

2. The prosthetic foot according to claim 1, further comprising an adapter connected to the proximal portion of the shank for use in connecting the prosthetic foot to a lower extremity prosthetic structure secured to a person's residual limb.

3. The prosthetic foot according to claim 1, wherein the anterior facing continuous convexly curved surface extends the entire length of the shank.

4. The prosthetic foot according to claim 1, wherein the monolithically formed shank and foot keel are formed of metal.

5. The prosthetic foot according to claim 1, wherein the monolithically formed shank and foot keel are formed of resilient material.

6. The prosthetic foot according to claim 1, wherein the width of the resilient shank in the frontal plane in the prosthetic foot is greater than the thickness of the shank in the sagittal plane throughout the entire length of the shank such that the shank, in response to a ground reaction force created in the prosthetic foot in gait, flexes substantially in the longitudinal direction of the foot keel for storing, releasing and directing energy in a longitudinal direction to improve dynamic response of the prosthetic foot.

7. A prosthetic foot comprising:
a continuously longitudinally extending foot having longitudinally aligned forefoot, raised midfoot, and hindfoot portions;
an ankle;
an elongated, upstanding shank adapted to extend above human ankle joint height and the ankle;
wherein the ankle, shank, and the entire foot are monolithically formed as a resilient member for improving the dynamic response of the prosthetic foot, the resilient member in the area of the ankle and shank being anterior facing convexly curved over the entire length of the ankle and shank of the resilient member above the foot, wherein the ankle extends upwardly from the raised midfoot portion of the foot, wherein the radius of curvature of the anterior facing convexly curved resilient member increases progressively as the resilient member extends upwardly from the foot, and wherein the resilient member provides means for sagital, anterior dorsiflexion and posterior plantarflexion motion capabilities in response to a ground reaction force created in a person's gait in the prosthetic foot.

8. The prosthetic foot according to claim 7, wherein the foot includes a continuously longitudinally extending foot keel which is monolithically formed with the ankle and shank as said resilient member.

9. The prosthetic foot according to claim 7, further comprising an adapter connected to a proximal portion of the resilient member for use in connecting the prosthetic foot to a lower extremity prosthetic socket on a person's leg stump.

10. The prosthetic foot according to claim 7, wherein the shank above the ankle is substantially curvilinear in the direction of the longitudinal extent of the foot.

11. The prosthetic foot according to claim 7, wherein the resilient member is formed of metal.

12. The prosthetic foot according to claim 7, wherein the resilient member is formed of plastic.

13. The prosthetic foot according to claim 7, wherein the width of the resilient member in the frontal plane in the prosthetic foot is greater than the thickness of the resilient member in the sagittal plane throughout the entire length of the resilient member such that the resilient member, in response to a ground reaction force created in the prosthetic foot in gait, flexes substantially in a longitudinal direction of the foot, for storing, releasing and directing energy in a longitudinal direction to improve dynamic response of the prosthetic foot.

* * * * *